United States Patent [19]

Oshiyama et al.

[11] Patent Number: 5,294,397
[45] Date of Patent: Mar. 15, 1994

[54] HEAT EXCHANGER FOR MEDICAL TREATMENT

[75] Inventors: Hiroaki Oshiyama; Atsuhiko Nogawa, both of Fuji, Japan

[73] Assignee: Terumo Kabushiki Kaisha, Tokyo, Japan

[21] Appl. No.: 876,899

[22] Filed: Apr. 29, 1992

Related U.S. Application Data

[60] Division of Ser. No. 726,623, Jun. 27, 1991, which is a continuation of Ser. No. 492,299, Feb. 28, 1990, abandoned, which is a division of Ser. No. 211,976, Jun. 27, 1988, abandoned.

[30] Foreign Application Priority Data

| Jun. 28, 1987 | [JP] | Japan | 1-60094 |
| Jul. 27, 1987 | [JP] | Japan | 1-87040 |
| Jul. 31, 1987 | [JP] | Japan | 1-16765[U] |
| Jul. 31, 1987 | [JP] | Japan | 1-16766[U] |
| Sep. 16, 1987 | [JP] | Japan | 1-40073[U] |

[51] Int. Cl.$^5$ ............................. B29C 39/10
[52] U.S. Cl. ................ 264/251; 264/254; 264/277
[58] Field of Search .................. 264/36, 251, 254, 277

[56] References Cited

U.S. PATENT DOCUMENTS

| 1,914,700 | 6/1933 | Mitchum | 165/118 |
| 2,837,855 | 6/1958 | Hoke | 264/254 X |
| 3,351,131 | 11/1967 | Berthold | 165/159 |
| 3,579,810 | 5/1971 | Mon | 264/277 X |
| 3,643,805 | 2/1972 | Hoffman | 264/277 X |
| 3,961,010 | 6/1976 | Holmes | 264/221 |
| 4,141,835 | 2/1979 | Schäel et al. | 210/456 |
| 4,177,816 | 12/1979 | Torgeson | 128/400 |
| 4,237,013 | 12/1980 | Yamazaki et al. | 210/456 |
| 4,288,310 | 9/1981 | Knight et al. | 264/251 X |
| 4,323,115 | 4/1982 | Stafford et al. | 165/79 |
| 4,352,772 | 10/1982 | Bezner | 264/229 |
| 4,424,190 | 1/1984 | Mather, III et al. | |
| 4,642,149 | 2/1987 | Harper | 165/160 |
| 4,689,191 | 8/1987 | Beck | 264/573 |
| 4,722,829 | 2/1988 | Giter | 422/46 |
| 4,740,344 | 4/1988 | Wollbeck | 264/248 |
| 4,789,473 | 12/1988 | Mathieu et al. | 210/456 |

FOREIGN PATENT DOCUMENTS

| 0081118 | 6/1983 | European Pat. Off. . | |
| 0167162 | 1/1986 | European Pat. Off. . | |
| 1501620 | 6/1969 | Fed. Rep. of Germany . | |
| 1479420 | 7/1969 | Fed. Rep. of Germany . | |
| 2356494 | 1/1978 | France | 264/277 |
| 2584609 | 6/1987 | France . | |
| 0103787 | 8/1979 | Japan | 210/321.8 |
| 55-134297 | 10/1980 | Japan . | |
| 0043804 | 11/1980 | Japan | 210/321.8 |
| 61-124638 | 8/1986 | Japan . | |
| WO86/02914 | 5/1986 | World Int. Prop. O. | 210/500.23 |

*Primary Examiner*—Allen J. Flanigan
*Attorney, Agent, or Firm*—Frishauf, Holtz, Goodman & Woodward

[57] ABSTRACT

A heat exchanger for medical treatment comprises a cylindrical blood passing space and a multiplicity of heat-exchanging tubes disposed inside the blood passing space and extending in the longitudinal direction of the blood passing space and provided with an inner space watertightly separated from the blood passing space for effecting exchange of heat between the blood being passed through the blood passing space and a heat-exchanging medium being passed through the inner spaces of the heat-exchnging tubes through the medium of walls of the heat-exchanging tubes. Blood inlet tube for introducing blood into the blood passing space and a blood outlet tube for discharging blood from within the blood passing space are expended inwardly from outside substantially along a straight lines perpendicular to the longitudinal direction of the blood passing space and tangent to the peripheral plane of the blood passsing space and communicating with the blood passing space. Optionally, the heat exchanger further comprises blood chambers disposed one each near the blood inlet and the blood outlet and each formed of an empty space destitute or devoid of the arrangement of the heat-exchanging tubes, and ribs formed on the inner wall of the blood passing space for retarding the flow of blood.

25 Claims, 10 Drawing Sheets

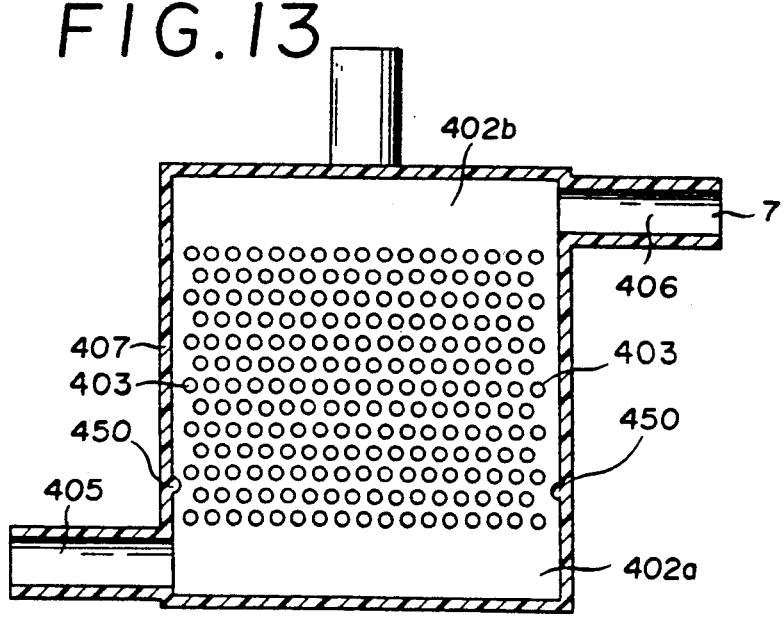
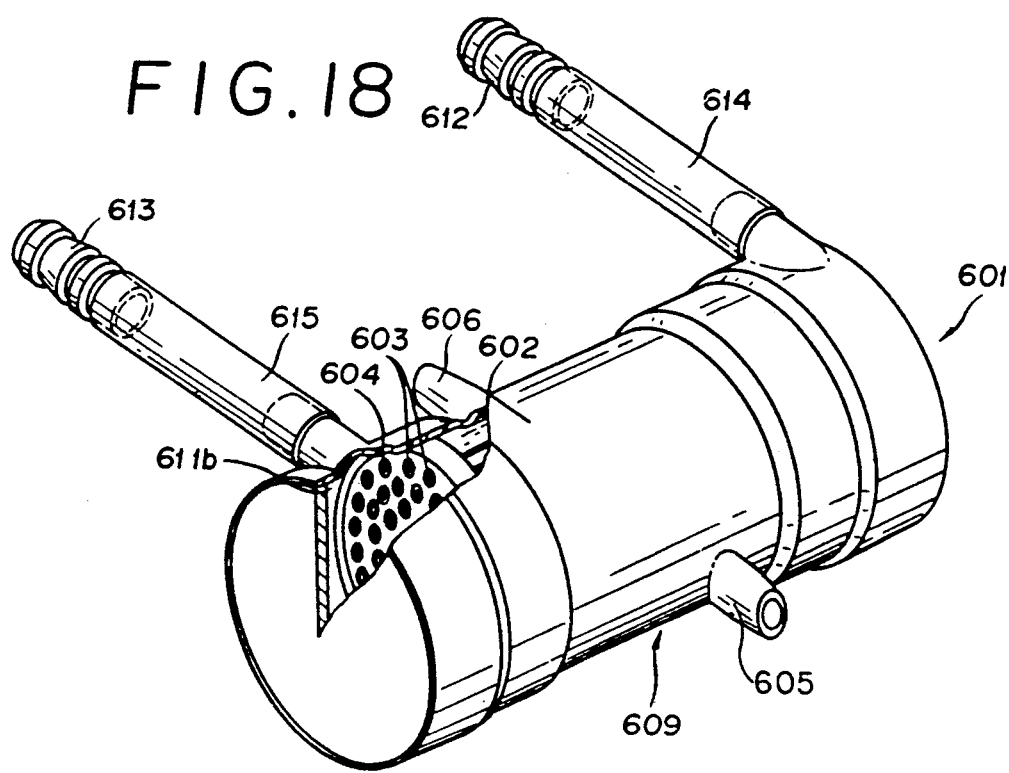

HEAT EXCHANGER FOR MEDICAL TREATMENT

This application is a division of application Ser. No. 07/726,623, filed Jun. 27, 1991, which is a continuation of Ser. No. 492,299 filed Feb. 28, 1990 (abandoned) which is a divisional of Ser. No. 07/211,976 filed Jun. 27, 1988 (abandoned).

BACKGROUND OF THE INVENTION

1. Field of the Invention

This invention relates to a heat exchanger for medical treatment. More particularly, it relates to a heat exchanger for medical treatment to be used in the extracorporeal circulation of blood for the purpose of maintaining the temperature of the blood at a desired level during the course of the circulation.

2. Description of the Prior Art

Extracorporeal blood circulation is generally employed as an auxiliary measure for surgery of the heart, particularly for cardiotomy. In the extracorporeal blood circulation as an auxiliary measure for cardiotomy, the blood drawn out of the patient's body is forwarded to an oxygenator, there to be oxygenated, and then returned in an oxygen-saturated state back to the patient's body. In the surgical operation performed on a complicated infantile cardiac deformation or on an adult aortic aneurysm, for example, the extremely low body temperature extracorporeal circulation method or the medial body temperature extracorporeal circulation method is employed. This blood circulation is effected by cooling the blood drawn out of the patient's body. In the extracorporeal body circulation of the nature under discussion, the blood drawn out of the patient's body must be kept at a prescribed temperature or cooled or heated. For this purpose, it has been customary to use a heat exchanger in the circuit for the extracorporeal blood circulation.

The heat exchangers developed to date for use in extracorporeal blood circulation are widely varied in type. For example, a shell-and-tube exchanger 1 which, as illustrated in FIGS. 1 and 2, comprises a first fluid passing space 2 and a multiplicity of heat-exchanging tubes 4 disposed inside the first fluid passing space 2 in the longitudinal direction of the first fluid passing space 2 and provided with an inner space 3 destined to form a second fluid passing space watertightly separated from the first fluid passing space 2 is a highly hopeful heat exchanger for medical treatment which effects very efficient exchange of heat and enjoys exceptional compactness of design. When the first fluid passing space 2 is formed in a cylindrical shape, a first fluid inlet tube 5 for introducing a first fluid into the first fluid passing space 2 and a first fluid outlet tube 6 for discharging the first fluid from the first fluid passing space 2 are adapted, as illustrated in FIGS. 1 and 2, so as to be extended inwardly from outside substantially along the straight line passing the central part of a cross section perpendicular to the axis of the first fluid passing space 2 and consequently allowed to communicate with the first fluid passing space 2.

When the shell-and-tube exchanger 1 constructed as described above is used in effecting exchange of heat between the blood and the heat-exchanging medium by passing the heat-exchanging medium through the first fluid passing space 2 and the blood through the second fluid passing space, i.e., the inner spaces 3 of the heat-exchanging tubes 4, the exchange of heat can be accomplished substantially uniformly on all of the blood because the blood is distributed comparatively uniformly and allowed to keep a relatively constant contact with respect to the heat-exchanging medium. When the pressure loss during the introduction of the blood is large and the extracorporeal blood circulation lasts for a long time, a fair possibility ensues that the blood will be coagulated inside the inner spaces 3 of the heat-exchanging tubes 4 and will consequently clog or constrict the heat-exchanging tubes 3. Conversely, when the exchange of heat is carried out by passing the blood through the first fluid passing space 2 and the heat-exchanging medium through the second fluid passing space or the inner spaces 3 of the heat-exchanging tubes 4, the aforementioned possibility of the blood conduits being clogged or constricted is substantially precluded and the pressure loss due to the introduction of the blood is repressed to a comparatively large extent. Since the first fluid inlet tube 3 and the first fluid outlet tube 6 are adapted, as described above, so as to be extended inwardly from outside substantially along the straight line passing the central part of a cross section perpendicular to the axis of the first fluid passing space 2 and consequently allowed to communicate with the first fluid passing space 2, the blood mainly advances toward the central part of the first fluid passing space 2 and consequently the flow of the blood inside the first fluid passing space 2 is not uniform but is varied locally. In the region of relatively high blood flow, exchange of heat is effected to an unduly small extent because the blood does not sufficiently contact the heat-exchanging tubes 4 now passing the heat-exchanging medium inside the inner spaces 3 thereof. By contrast, in the region of relatively low blood flow, the exchange of heat is effected to an unduly large extent because the blood contacts the heat-exchanging tubes 4 more than is normally required. Where the heat-exchanging tubes 4 are distributed throughout the whole blood passing space 2 as illustrated in FIGS. 1 and 2, the unfavorable situation mentioned above grows in conspicuity because the blood introduced through the blood inlet tube 5, on entering the blood passing space 2, comes into direct contact with the heat-exchanging tubes 4 and, consequently, the blood flow is not uniformly distributed throughout the entire blood passing space 2. The shell-and-tube exchanger which is incapable of effecting exchange of heat uniformly on all of the blood being passed therethrough thus, there is the possibility of impairing the uniformity of blood temperature distribution, exchanging heat excessively or insufficiently, exchanging heat and bringing about adverse effects upon the blood components.

Further, the conventional heat exchanger is so constructed that a heat-exchanging medium inlet port for introducing the heat-exchanging medium into the heat exchanger and a heat-exchanging medium outlet port for discharging the heat-exchanging medium from within the heat exchanger are integrally formed with a housing of the heat exchanger and are fixed on the housing. A connection tube which leads out of a heat-exchanging medium temperature controller communicating with the heat-exchanging medium inlet port and the heat-exchanging medium outlet port is generally large in diameter and hard to the touch. The connection between the coupler disposed on the heat-exchanging medium inlet port or the heat-exchanging medium outlet port and the coupler disposed at the leading end of the connection tube of the heat-exchanging medium temperature controller is obtained only with difficulty. Moreover, the possibility ensues that this connection will be dissolved in consequence of a deviation suffered to occur in the positional relationship between the heat exchanger and the heat-exchanging medium temperature controller during the course of operation.

An object of this invention, therefore, is to provide an improved heat exchanger for medical treatment.

Another object of this invention is to provide a heat exchanger for medical treatment which, in extracroporeal blood circulation, enables the blood drawn out of a patient's body to be kept at a desired temperature.

Yet another object of this invention is to provide a heat exchanger for medical treatment which effects uniform exchange of heat between the blood and the heat-exchanging medium and inflicts damage sparingly on the blood under treatment.

Still another object of this invention is to provide a heat exchanger for medical treatment which enjoys exceptional compactness of design and suffers from only a small pressure loss during the introduction of blood.

A further object of this invention is to provide a heat exchanger for medical treatment which is capable of being integrated with an oxygenator.

A still further object of this invention is to provide a heat exchanger for medical treatment which excels in operability and ensures great safety.

SUMMARY OF THE INVENTION

The objects of this invention described above are accomplished by a heat exchanger for medical treatment comprising a cylindrical blood passing space and a multiplicity of heat-exchanging tubes disposed inside the blood passing space in the longitudinal direction of the blood passing space and provided with an inner space watertightly separated from the blood passing space and effecting exchange of heat between the blood being passed through the blood passing space and a heat-exchanging medium being passed through the inner spaces of the heat-exchanging tubes through the medium of walls of the heat-exchanging tubes, characterized by the fact that a blood inlet tube for introducing blood into the blood passing space and a blood outlet tube for discharging blood from within the blood passing space are extended inwardly from outside substantially along straight lines perpendicular to the longitudinal direction of the blood passing space and tangent to the peripheral plane of the blood passing space and allowed to the peripheral plane of the blood passing space and allowed to communicated with the blood passing space.

This invention also relates to a heat exchanger for medical treatment which comprises a multiplicity of heat-exchanging tubes disposed as mutually separated inside a cylindrical housing possessing closed opposite ends in the longitudinal direction of the housing, partition walls disposed at the opposite end parts of the heat-exchanging tubes to hold the heat-exchanging tubes fast watertightly on the lateral wall of the housing without closing the openings of the heat-exchanging tubes and, at the same time, to partition the interior of the housing into three spaces, a blood inlet tube and a blood outlet tube severally extended inwardly from outside substantially along straight lines perpendicular to the longitudinal direction of the housing and tangent to the peripheral surface of the housing to communicate with a blood passing space formed in the central part of the housing by the two partition walls, the lateral wall of the housing, and the outer walls of the heat-exchanging tubes, and a heat-exchanging medium inlet tube to communicate with one of two heat-exchanging medium passing spaces formed at the end parts of the housing communicating with the inner spaces of the heat-exchanging tubes watertightly separated from the blood passing space and a heat-exchanging medium passing space. This invention further relates to a heat exchanger for medical treatment wherein the blood inlet tube communicates with the blood passing space in the proximity of one of the partition walls and the blood outlet tube communicates with the blood passing space in the proximity of the other partition wall.

This invention still further relates to a heat exchanger for medical treatment wherein the blood inlet tube and the blood outlet tube assume a positional relation such that they are rotated by about 180° from each other around the peripheral surface of the blood passing space.

The objects of this invention described above are accomplished by a heat exchanger for medical treatment comprising a cylindrical blood passing space and a multiplicity of heat-exchanging tubes disposed inside the blood passing space in the longitudinal direction of the blood passing space and provided with an inner space watertightly separated from the blood passing space and effecting exchange of heat between the blood being passed through the blood passing space and a heat-exchanging medium being passed through the inner spaces of the heat-exchanging tubes through the medium of walls of the heat-exchanging tubes, a blood inlet tube for introducing blood into the blood passing space and a blood outlet tube for discharging blood from the blood passing space are extended inwardly from outside substantially along straight lines perpendicular to the longitudinal direction of the blood passing space and tangent to the peripheral place of the blood passing space and communicating with the blood passing space. The heat-exchanging tubes are disposed so as to be uniformly separated mutually throughout the entire blood passing space except for an empty space portion formed by extending in the axial direction of the blood passing space a portion enclosed in the shape of a bow possessing a chord substantially parallel to and equal to or slightly longer than a line segment connecting two points of intersection between two inner peripheral lines of the blood inlet tube and the circumference of the blood passing space in a cross section perpendicular to the axis of the blood passing space inclusive of the axial line of the blood inlet tube and an empty space portion formed by extending in the axial direction of the blood passing space a portion enclosed in the shape of a bow possessing a chord substantially parallel to and equal to or slightly longer than a line segment connecting two points of intersection between two inner peripherarl lines of the blood outlet tube and the circumference of the blood passing space in a cross section perpendicular to the axis of the blood passing space inclusive of the axial line of the blood output tube.

This invention further relates to a heat exchanger for medical treatment which comprises causing a multiplicity of heat-exchanging tubes disposed as mutually separated inside a cylindrical housing possessing closed opposite ends in the longitudinal direction of the housing, partition walls disposed at the opposite end parts of the heat-exchanging tubes to hold the heat-exchanging tubes fast watertightly on the lateral wall of the hosuing without closing the openings of the heat-exchanging tubes and, at the same time, to partition the interior of the housing into three spaces, a blood inlet tube and a blood outlet tube to communicate with a blood passing sapce formed in the central part of the housing by the two partition walls, the lateral wall of the hosuing, and the outer walls of the heat-exchanging tubes, and a heat-exchanging medium inlet tube to communciate with one of two heat-exchanging medium passing spaces formed at the end parts of the housing communicating with the inner spaces of the haet-exchanging tubes watertightly separated from the blood passing space and a heat-exchanging medium outlet tube to communicate with the other heat-exchanging medium passing space. This invention also relates to a heat exchanger for medical treatment wherein the blood inlet tube communicates with the blood passing space in the proximity of one of the partition walls and the blood outlet tube communicates with the blood passing space in the proximity of the other partition wall.

This invention further relates to a heat exchanger for medical treatment wherein the blood inlet tube and the blood outlet tube assume a positional relation such that they are rotated by about 180° from each other around the peripheral surface of the blood passing space.

Further, this invention relates to a heat exchanger for medical treatment wherein the two empty space portions destitute of arrangement of heat-exchanging tubes within the blood passing space occupy a total volume of less than 40% of the blood passing space.

The objects of this invention described above are accomplished by a heat exchanger for medical treatment comprising a cylindrical housing possessing a blood inlet and a blood outlet, a multiplicity of slender heat-exchanging tubes accommodated within the cylindrical housing, partition walls adapted to fix the opposite end parts of the slender heat-exchanging tubes watertightly to the cylindrical housing and partition the interior of the hosuing into a blood chamber communicating with the blood outlet and the blood inlet and a heat-exchanging medium chamber formed by the tube interiors, and a medium inlet and a medium outlet communicating with the heat-exchanging medium chamber, which comprises at least one rib formed on the inner wall surface of the housing extended panel to the slender tubes opposed to the inner wall surface and adapted to retard the flow of blood between the slender tubes and the inner wall surface of the housing. This heat exchanger is desired to possess a space destitute of the slender tubes near the position of the housing at which the blood inlet is located. Optionally, the blood inlet may be fitted as directed toward the inner wall side of the housing at a stated angle from the center of the housing. The heat exchanger is desired to possess a space destitute of the slender tubes near the position of the housing at which the blood outlet is located. Optionally, the blood outlet may be fitted as directed toward the inner wall side of the housing at a stated angle from the center of the housing. Further, the blood inlet is desired to be fitted as directed toward the inner wall side of the housing at a stated angle from the center of the housing and the ribs to be formed on the inner surface of the housing toward which the blood inlet is directed. Further, the blood outlet may be disposed substantially parallel to the direction of the blood inlet. Further, a multiplicity of slender tubes are desired to be accomodated as separated mutually by a substantially uniform distance inside the housing and the distance between the ribs and the slender tubes approximating the ribs to be smaller than the distance between the slender tubes. Further, the ribs are desired to be disposed near those of the slender tubes which are located in the neighborhood of the blood inlet. The housing is formed in a substantially cylindrical shape, for example. The heat exchanger may be provided with a plurality of ribs.

The objects of this invention described above are further accomplished by a heat exchanger for medical treatment which comprises an integrally molded cylindrical housing possessing a heat-exchanging medium inlet port disposed at one end part thereof, a heat-exchanging medium outlet port dispoed at the other end part thereof, and a blood inlet port and a blood outlet port disposed at positions between the medium inlet port and the medium outlet port, a multiplicity of slender heat-exchanging tubes accomodated within the housing, partitin walls adapted to fix the opposited end aprts of the slender tubes watertightly to the cylindrical housing and partition the interior of the housing into a blood chamber communiating with the blood outlet port and the blood inlet port and a heat-exchanging medium chamber formed inside the tubes and adapted to communicate with the medium inlet port and the medium outlet port, and sealing members serving to seal the opposite end parts of the housing.

The heat exchanger just described is desired to possess a space destitute or devoid of the slender tubes near the position of the housing at which the blood inlet, port is located. It is further desired to provide a space destitute or devoid of the slender tubes near the position of the housing at which the blood outlet port is located. The housing is formed in a cylindrical shape, for example. The partition walls are formed of a potting compound, for example. The partition walls comprise perforated plates adapted to keep hold of the end parts of the slender tubes and a potting compound for watertightly fixing the perforated plates to the slender tubes. The perforated plates are desired each to possess a multiplicity of holes formed in a shape such that the inside diameter of hole at one end is larger than the outside diameter of the slender tubes and at the other end smaller then the outside diameter of the slender tubes. Further, the medium inlet port is desired to be fitted as directed toward the inner surface side of the housing at a stated angle from the center of the housing. Further, the medium inlet port is desired to be fitted in a direction substantially tangent to the outer surface of the housing. Further, the medium inlet port is desired to be fitted in a direction substantially tangent to the outer surface of the housing. The medium outlet port may be fitted as directed toward the inner surface side of the housing at a stated angle from the center of the housing. The medium outlet port, for example, is fitted in a direction substantially tangent to the outer surface of the housing.

The objects of this invention described above are further accomplished by a method for the production of a heat exchanger for the blood under treatment by the extracorporeal circulation, which comprises the steps of forming a cylindrical housing possessing heat-exchanging medium ports disposed one each at the opposite end parts thereof and a blood inlet port and a blood outlet port disposed at positions between the medium ports, attaching a first sealing member at a position between those of the medium ports and the blood ports which are located at one end part of the cylindrical housing, inserting through the other end part of the cylindrical housing into the cylindrical housing a slender tube distibuting device possessing a multiplicity of holes for insertion of slender heat-exchanging tubes and a multiplicity of slender heat-exchanging tubes, attaching a second sealing member at a position between those of the medium ports and the blood ports which are located at the other end part of the cylindrical housing, injecting a potting compound through the blood port on one end part side and the blood port on the other end part side of the cylindrical housing with the end parts of the slender heat-exchanging tubes kept in a closed state thereby forming partition walls for fixing the opposite end parts of the slender heat-exchanging tubes to the cylindrical housing, removing the first sealing member and the second sealing member, and fitting seal members one each to the opposite ends of the cylindrical housing.

The insertion of the slender tube distributing device possessing a multiplicity of holes for insertion of slender heat-exchanging tubes and a multiplicity of slender heat-exchanging tubes through the other end part of the cylindrical housing into the cylindrical hosuing is carried out, for example, while keeping the cylindrical hosuing set upright on the one end part of the cylindrical housing to which the first sealing member has been attached. Otherwise, the insertion of the slender tube distributing device possessing a multiplicity of holes for insertion of slender heat-exchanging tubes and a multiplicity of slender heat-exchanging tubes through the other end part of the cylindrical housing into the cylindrical housing is carried out, for example, by a procedure which comprises first inserting through the other end part of the cylindrical housing into the cylindrical housing the slender tube-distributing device possessing a multiplicity of holes for insertion of slender heat-exchanging tubes and subsequently inserting the multiplicity of slender heat-exchanging tubes. The formation of partition walls for fixing the opposite end parts of the slender heat-exchanging tubes to the cylindrical housing by the injection of a potting compound through the blood port on one end part side and the blood port on the other end part side of the cylindrical housing with the end parts of the slender heat-exchanging tubes kept in a closed state is accomplished, for example, by injecting the potting compound through the blood port on one end part side of the cylindrical housing, then turning the cylindrical hosuing upside down, injecting the potting compound through the blood port on the other end part side of the cylindrical housing, and allowing the injected portions of the potting compound to set and give rise to partition walls. Further, the formation of partition walls for fixing the opposite end parts of the slender heat-exchanging tubes to the cylindrical housing by the injection of a potting compound through the blood port on one end part side and the blood port on the other end part side of the cylindrical housing with the end parts of the slender heat-exchanging tubes kept in a closed state is accomplished, for example, by injecting the potting compound through the blood port on one end part side of the cylindrical housing, allowing the injected portion of the potting compound to set, then removing the second sealing member and the slender tube-distributing device, attaching the second sealing member, injecting the potting compound through the blood port on the other end part side of the cylindrical housing with the end parts of the slender heat-exchanging tubes kept in a closed state, and allowing the injected portion of the potting compound to set.

The step of removing the first sealing member and the second sealing member and the step of attaching the seal members one each to the opposite ends of the cylindrical housing are carried out, for example, by a procedure which comprises first removing the first sealing member and the second sealing member and subsequently attaching the seal members one each to the opposite end parts of the cylindrical housing. Further, the step of removing the first sealing member and the second sealing member and the step of attaching the seal members one each to the opposite ends of the cylindrical housing are carried out, for example, by a procedure which comprises a step of removing either the first sealing member or the second sealing member and attaching one of the seal members to the end part from which the sealing member has been removed and a step of removing the remaining sealing member and attaching the remaining seal member to the end part from which the remaining sealing member has been removed. Further, the first sealing member is desired to comprise an elastic sealing member and an assembly retaining device for retaining the elastic sealing member in place.

The objects of this invention described above are further accomplished by a heat exchanger for medical treatment comprising a housing for enclosing a closed empty space therewith and heat-exchanging tubes disposed inside the housing and provided each with an inner space watertightly separated from the closed empty space and effecting exchange of heat between a first fluid passed through the inner spaces of the heat-exchanging tubes and a second fluid passed through the closed empty space of the housing through the medium of walls of the heat-exchanging tubes, which heat exchanger is characterized by the fact that a heat-exchanging medium inlet port and a heat-exchanging medium outlet port for causing the first fluid or the second fluid intended as a heat-exchanging medium to be respectively introduced into and discharged from the inner spaces of the heat-exchanging tubes disposed inside the housing or the closed emtpy space of the housing are extended from the outer wall surface of the housing with flexible tubes.

BRIEF DESCRIPTION OF THE DRAWINGS

FIG. 13 is a cross section of still yet another embodiment, FIG. 18 is a perspective view of still another embodiment of the heat exchanger of the present invention.

DESCRIPTION OF THE PREFERRED EMBODIMENTS

Figure 3:
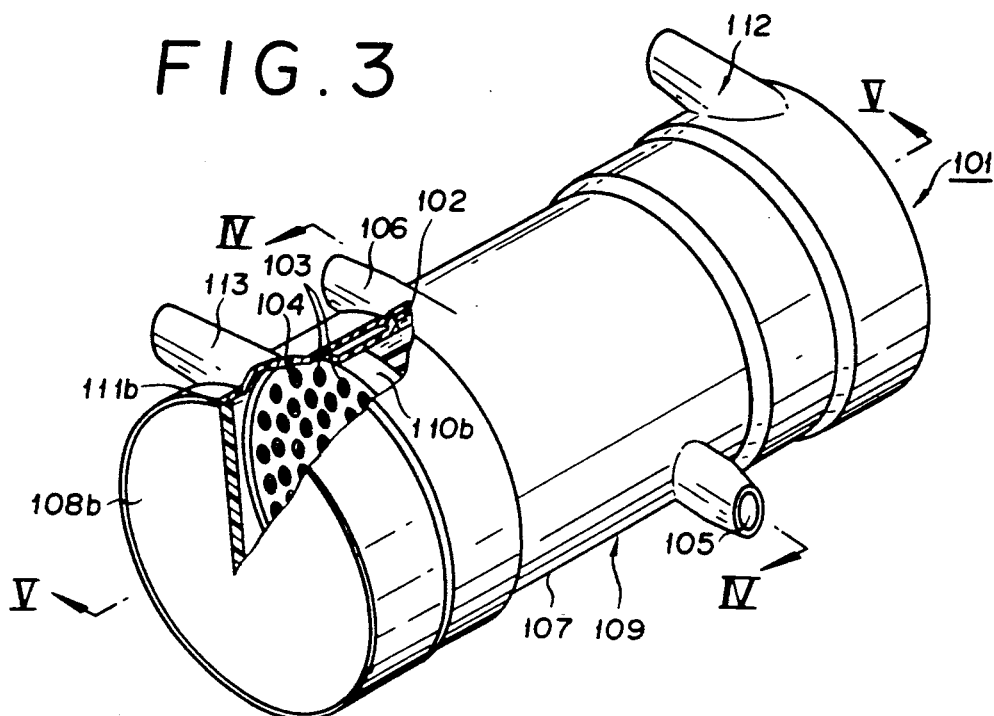
FIG. 3 is a partially cutaway perspective view illustrating a typical heat exchanger for medical treatment as one embodiment of the present invention.
Figure 4:
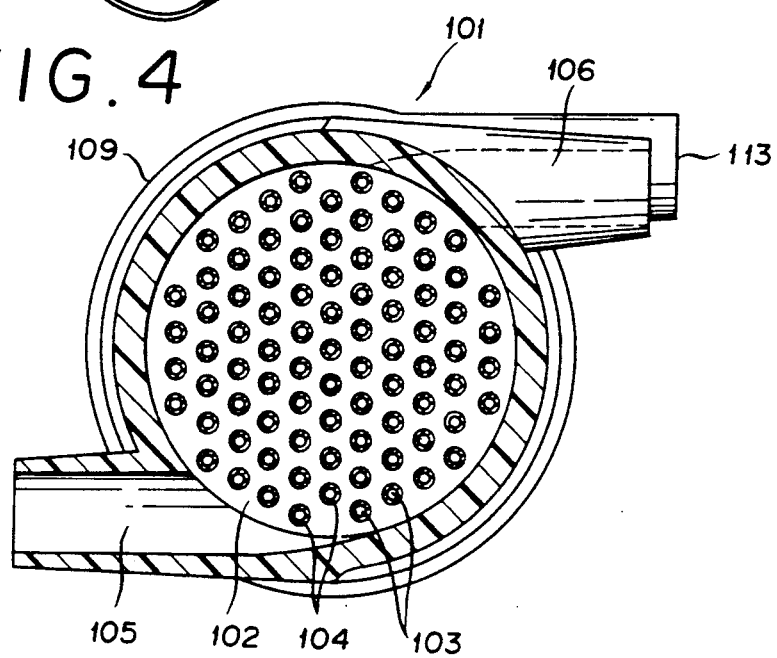
FIG. 4 is a cross section taken through FIG. 3 along the line IV—IV.
Figure 5:
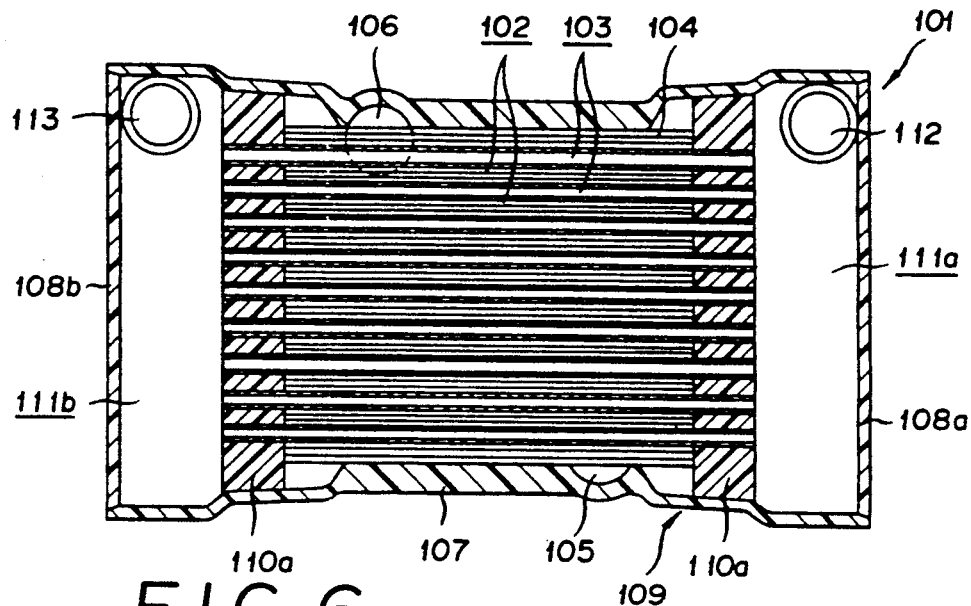
FIG. 5 is a cross section taken through FIG. 3 along the line V—V.

A heat exchanger 101 of this invention for medical treatment, as illustrated in FIGS. 3 to 5, comprises a cylindrical blood passing space 102 and a multiplicity of heat-exchanging tubes (i.e., slender tubes) 104 disposed inside the cylindrical blood passing space 102 along the longitudinal direction of the blood passing space 102 and each provided with an inner space watertightly separated from the blood passing space 102 and effects exchange of heat across the walls of the heat-exchanging tubes 104 between the blood passed through the blood passing space 102 and a heat-exchanging medium passed through the inner spaces 103 of the heat-exchanging tubes 104. This heat exchanger 101 has as a salient characteristic thereof the fact that a blood inlet tube (i.e., blood port) 105 for introducing blood into the blood passing space 102 and a blood outlet tube (i.e., blood port) 106 for discharging the blood from the blood passing space 102 are severally extended inwardly from outside substantially along straight lines perpendicular to the longitudinal direction of the blood passing space 102 and tangent to the peripheral surface of the blood passing space 102 and communicating with the blood passing space 102.

When the blood inlet tube 105 and the blood outlet tube 106 are extended inwardly from outside substantially along straight lines perpendicular to the longitudinal direction of the blood passing space 102 and communication with the blood passing space 102 and described above, the blood introduced through the blood inlet tube 105 is induced to assume a flow tending to revolve inside the blood passing space 102 along the periphery of the blood passing space 102 and the blood passed through the interior of the blood passing space 102 is caused to come into uniform contact with substantially all the heat-exchanging tubes 104 disposed inside the blood passing space 102 except mainly for a specific group of heat-exchanging tubes 104 which are located in the central part of the blood passing space 102, namely on a roughly straight line connecting the communicating entrance to the blood inlet tube 105 and the communicating entrance to the blood outlet tube 106. Thus, the exchange of heat is attained uniformly within the blood passing space 102 without entailing any locally excessive or insufficient exchange of heat. Further in the heat exchanger of this invention, since the blood is passed outside the heat-exchanging tubes 104, it is neither compelled to find only a limited flow path during the course of introduction thereof into the blood passing space 102 nor forced to suffer from any large pressure loss or entail any heavy damage to the blood components.

The heat exchanger for medical treatment in the present embodiment is so constructed that inside a cylindrical housing 109 of closed opposite ends formed of a housing proper 107 and end plates 108a, 108b closing the open opposite ends thereof as illustrated in FIGS. 3 to 5, the multiplicity of heat-exchanging tubes 104 are disposed so as to be mutually separated along the longitudinal direction of the housing 109 and partition walls 110a, 110b disposed one each at the opposite end parts of the plurality of heat-exchanging tubes 104 retain the heat-exchanging tubes 104 watertightly to the lateral wall of the housing 109 without closing the openings of the heat-exchanging tubes 104. At the same time, these partition walls 110a, 110b serve the purpose of partitioning the interior of the housing 109 into three empty spaces. The central portion of the housing 109 enclosed with the two partition walls 110a, 110b, the lateral wall of the housing 109, and the outer walls of the heat-exchanging tubes 104 constitutes itself the blood passing space 102 and the two end portions of the housing 109 watertightly separated from the blood passing space 102 and enclosed with the partition walls 110a, 110b and the end part walls and the lateral wall of the housing 109 constitute themselves the heat-exchanging medium passing spaces 111a, 111b. These two heat-exchanging medium passing spaces 111a, 111b both communicate with the inner spaces 103 of the heat-exchanging tubes 104 which are watertightly separated from the blood passing space 102. In the construction formed as described above, the blood inlet tube 105 and the blood outlet tube 106 communicate with the blood passing space 102 and the heat-exchanging medium outlet tube 112 communicates with the heat-exchanging medium passing space 111a and the heat-exchanging medium inlet tube 113 with the other heat-exchanging medium passing space 111b.

Further, in the heat exchanger 101 of the present embodiment for medical treatment, the blood inlet tube 105 and the blood outlet tube 106 are extended inwardly from outside substantially along straight lines perpendicular to the longitudinal direction of the housing 109 and tangent to the peripheral surface of the housing 109, namely substantially along straight lines perpendicular to the longitudinal direction of the blood passing space 102 and tangent to the peripheral surface of the blood passing space 102, and consequently allowed to communicate with the blood passing space 102. The blood inlet tube 105 and the blood outlet tube 106 which are extended inwardly from outside need not fall exactly on the straight lines perpendicular to the longitudinal direction of the blood passing space 102 and tangent to the peripheral surface of the blood passing space 102 but may deviate from the straight lines to an extent such that they will not be prevented from effectively imparting to the blood passed through the blood passing space 102 a flow along the peripheral surface of the blood passing space 102. Further, the blood inlet tube 105 and the blood outlet tube 106 are only required, at least in the portions thereof immediately before their points of communication with the blood passing space 102, to run roughly along the straight lines perpendicular to the longitudinal direction of the blood passing space 102 and tangent to the peripheral surface of the blood passing space 102. For the subsequent portions thereof, the directionality is a matter for arbitrary decision. The positions at which the blood inlet tube 105 and the blood outlet tube 106 are to be located are not specifically defined. For the purpose of ensuring effective exchange of heat between the heat-exchanging medium passed through the inner spaces of the heat-exchanging tubes 104 inserted inside the blood passing space 102 and the blood passed through the blood passing space 102, they must be allowed to communicate with the blood passing space 102 at mutually separated positions. Desirably, as illustrated in FIGS. 3-5, the blood inlet tube 105 is allowed to communicate with the blood passing space 102 near one of the partition walls 110a and 110b and the blood outlet tube 106 to communicate with the blood passing space 102 near the other partition walls 110a or 110b. Further, the blood inlet tube 105 and the blood outlet tube 106 are desired to assume a positional relation such that they are rotated by about 180° from each other around the peripheral surface of the blood passing space 102 as illustrated in FIGS. 3 and 4.

The heat exchanger 101 for medical treatment of the present embodiment which is constructed as described above is put to use as incorporated suitably in a varying extracorporeal circulation circuit. Since it is featured by exceptional compactness of design asnd high performance, it can be advantageously utilized as integrated with an oxygenator and a blood storing tank and operated as an oxygenator system as illustrated in FIGS. 6 and 7, for example.

Figure 6:
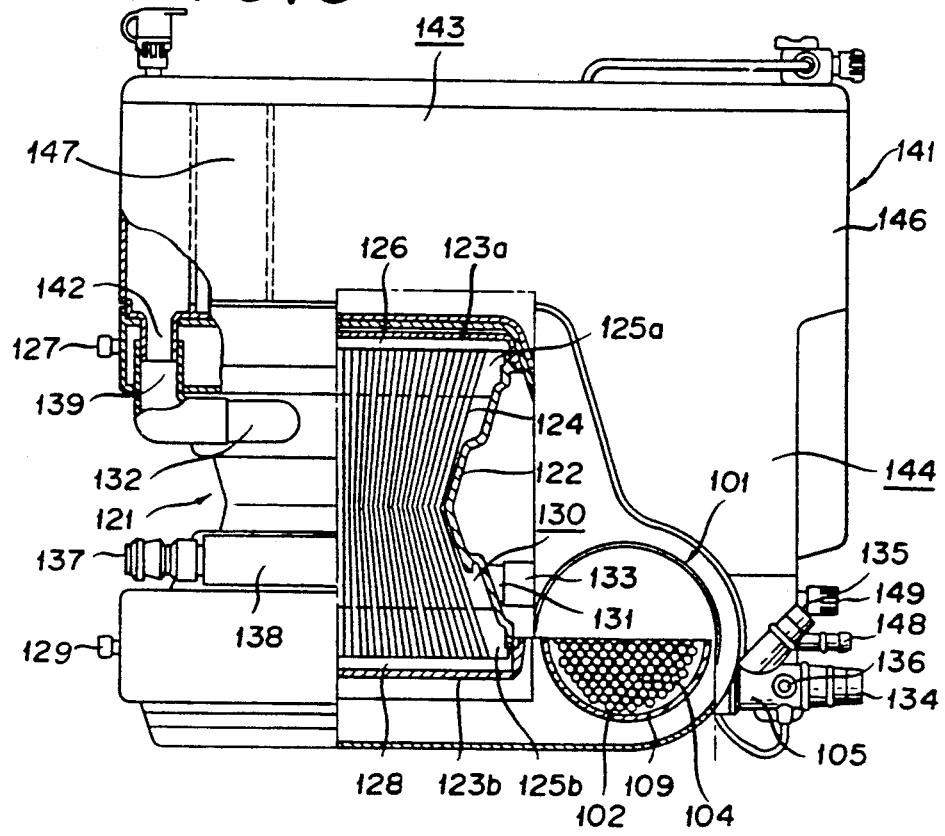
FIG. 6 is a partially sectioned front view of an oxygenator incorporating therein the heat exchanger of the present invention.
Figure 7:
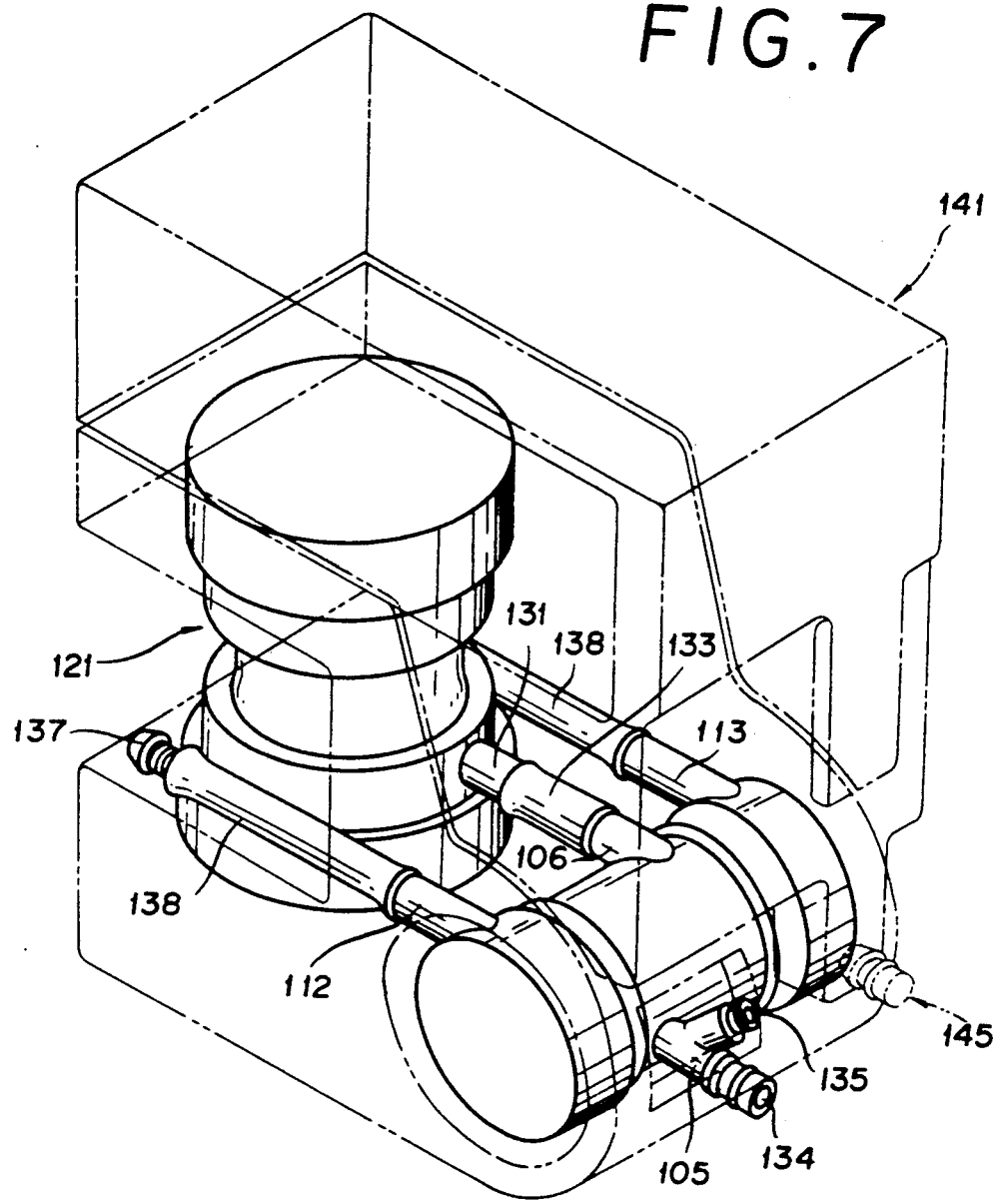
FIG. 7 is a perspective view of the oxygenator illustratd in FIG. 6.

In the embodiment illustrated in FIGS. 6 and 7, an oxygenator 121 is provided with a housing which comprises a cylindrical housing body 122 and fitting covers 123a, 123b closing the open opposite end parts of the housing body 122. Inside the housing, a multiplicity of hollow fiber membranes 124 are paralelly disposed so as to be mutually separated along the longitudinal direction of the housing and distributed cross-sectionally throughout the entire interior of the housing. The opposite end parts of these hollow fiber membranes 124 are watertightly retained on the housing body 122 by means of partition walls 125a, 125b, with the openings of the opposite end parts kept in an opened state. A gas inlet port 127 is disposed so as to communicate with a gas inelt space 126 defined by the fitting cover 123a, the housing body 122, and the partition wall 125a and allowed to communicate with the inner spaces of the hollow fiber membranes and a gas passing port 129 is disposed so as to communicate with a gas passing space 128 defined by the other fitting cover 123b, the housing body 122, and the partition wall 125b and allowed to communicate with the inner spaces of the hollow fiber membranes. Further, a blood inlet tube 131 and a blood outlet tube 132 are disposed so as to communicate with a blood chamber 130 formed of the inner wall of the housing body 122, the two partition walls 125a, 125b, and the outer walls of the hollow fiber membranes 124.

The oxygenator 121 illustrated in the present embodiment is of a type which effets exchange of gas by blowing an oxygen-containing gas such as air into the inner spaces of the hollow fiber membranes and passing blood outside the hollow fiber membranes 124. Otherwise, the oxygenator may be constructed as a type which effects the exchange of gas by passing blood in the inner spaces of the hollow fiber membranes and a passing the oxygen-containing gas outside the hollow fiber membranes. Alternatively, an oxygenator of a type using flat gas-exchange membranes is also available. In all these types of oxygenators, particularly desirable is the type which passes the blood outside the hollow fiber membranes as illustratd in the present embodiment. Since the oxygenator of this type has very little pressure loss, the oxygenator system using his oxygenator need not be provided with a blood pump in front of the oxygenator inserted in the path of circulation circuit. It has only to rely upon the removal of blood from a patient's body owing to the head of pressure to obtain required flow of the blood to the oxygenator and further to the blood storing tank.

The blood outlet tube 106 of the heat exchanger 101 for medical treatment is allowed to communicate watertightly with the blood inlet tube 131 of the oxygenator 121 through the medium of a connection tube 133 as illustrated in FIG. 7. The watertight connection of the connection tube 133 to the blood inlet tube 131 of the oxygenator 121 and to the blood outlet tube 106 of the heat exchanger 101 for medical treatment is attained by tight fitting by the use of a screw, a taper, or an O-ring or by tight adhesion by means of ultrasonic waves or high-frequency waves or by means of an adhesive agent. Of course, it is permissible to connect the blood inlet tube 131 of the oxygenator 121 directly and watertightly to the blood outlet tube 106 of the heat exchanger 101 for medical treatment by similar means of connection. The exchanger for medical treatment in the present embodiment and illustrated in FIGS. 3 to 5 are substantially identical, though they differ slightly with respect to the positions at which the blood inlet tube 105 and the blood outlet tube are located. The blood inlet tube 105 in the heat exchanger 101 for medical treatment in the present embodiment is provided with a cardiotomy inlet port 135 for introduction of the blood shed during the course of surgical operation in addition to a blood inlet port 134 for connection to the extracorporeal circulation path. The blood inlet tube 105 of this heat exchanger 101 is provided with a temperature measuring probe insertion hole 136. To the heat-exchanging medium inlet tube 113 and the heat-exchanging medium outlet tube 112, flexible extension tubes 138 provided at the leading end part thereof with a water inlet port (not shown) or a water outlet port 137 are connected.

In the meantime, a blood inlet 142 of a blood storing tank 141 is connected watertightly with a connection tube 139 to the blood outlet tube 132 of the oxygenator 121. The watertight connection of the connection tube 139 to the blood outlet tube of the oxygenator 121 and to the blood inlet tube 142 of the blood storing tank 141 is attained in the same manner as in the watertight connection of the connection tube 133 to the blood inlet tube 131 of the oxygenator 121 and to the blood outlet tube 106 of the heat exchanger 101 for medical treatment.

With a housing 146 made of rigid material and provided with a blood inlet 142, a blood inlet part 143 communicating with the blood inlet 142 and possessing a bottom surface having substantially no head of pressure from the blood inlet 142, a blood storing part 144 communicating with the blood inlet part 143 and possessing a bottom surface destined to fall gradually from the blood inlet part 143, and a blood outlet 145 disposed below the blood storing part 144, the blood storing tank 141 which is connected to the oxygenator 121 is formed by disposing a defoaming member 147 across the entire width of the blood flow path of the blood inlet part 143. This blood storing tank 141 is provided not only with the blood outlet 145 connected to the extracorporeal circulation path but also with a cardio-pregear part 148 destined to be connected to the path for forwarding blood to the cardiac vein and adapted to communicated with the lower part of the blood storing part 144. It is further provided with a temperature measuring probe insertion port 149 intended to measure the temperature of blood within the blood storing tank 141.

In the oxygenator system which integrates the heat exchanger 101 for medical treatment and the blood storing tank 147 with the oxygenator 121 as described above, the blood withdrawn from a patient's body flows into the heat exchanger 101 via the blood inlet tube 105. Since the blood inlet tube 105 and the blood outlet tube 106 are extended inwardly from outside substantially along the straight lines perpendicular to the longitudinal direction of the blood passing space 102 and tangent to the peripheral surface of the blood passing space 102 and allowed to communicate with the blood passing space 102 as described above, the blood introduced through the blood inlet tube 105 into the blood passing space 102 is induced to generate a flow tending to revolve inside the blood passing space 102 along the inner peripheral surface of the blood passing space 102 and the blood passed through the interior of the blood passing space 102 is brought into uniform contact with substantially all the heat-exchanging tubes 104 disposed inside the blood passing space 102, except mainly for the specific group of heat-exchanging tubes 104 which are located in the central part of the blood passing space 102, namely on the roughly straight line connecting the point of communication with the blood inlet tube 105 and the point of communication with the blood outlet tube 106. As the result, the exchange of heat across the walls of the heat-exchanging tubes within the blood passing space 102 between the blood and the water, i.e. a heat-exchanging medium, which is introduced through the heat-exchanging medium inlet tube 113 into the heat-exchanging medium passing space 111b, passed through the inner spaces 103 of the heat-exchanging tubes 104 to the heat-exchanging medium passing space 111a, and discharged through the heat-exchanging medium outlet tube 112 is carried out efficiently and uniformly. The blood which has been heated or cooled to a desired temperature is led out of the heat exchanger 101 through the blood outlet tube 106 and then forwarded to the oxygenator 121 through the blood inlet tube 131 of the oxygenator 121 communicating watertightly with the blood outlet tube 106. The blood which has flowed into the oxygenator 121 via the blood inlet tube 131, while flowing through the blood chamber 130, exchanges gas through the medium of the walls of the hollow fiber membranes 124 with the oxygen-containing gas which is flowing through the inner spaces of the hollow fiber membranes 124. Consequently, the blood is divested of excess carbon dioxide gas and instead replenished with fresh oxygen. The blood which has been oxygenated flows out of the blood outlet tube 132 of the oxygenator 121 and then continues its flow into the blood storing tank 141 through the blood inlet 142 of the blood storing tank 141. The blood which has flowed from the blood inlet 142 to the blood inlet part 143 communicating therewith and reached the defoaming member 147 disposed in route to the blood inlet part 143 is defoamed during the course of its passage through the defoaming member 147 by the fact that the bubbles entrained by the blood come into contact with the foam cells of the defoaming member 147, gradually agglomerate, and depart from the blood and move to the upper empty space inside the blood storing tank 141. The defoamed blood further moves to the blood storing part 144, remains temporarily in the blood storing part 144, releases itself through the blood outlet 145 disposed below the blood storing part 144, and finds its way to the patient's body.

Figure 8:
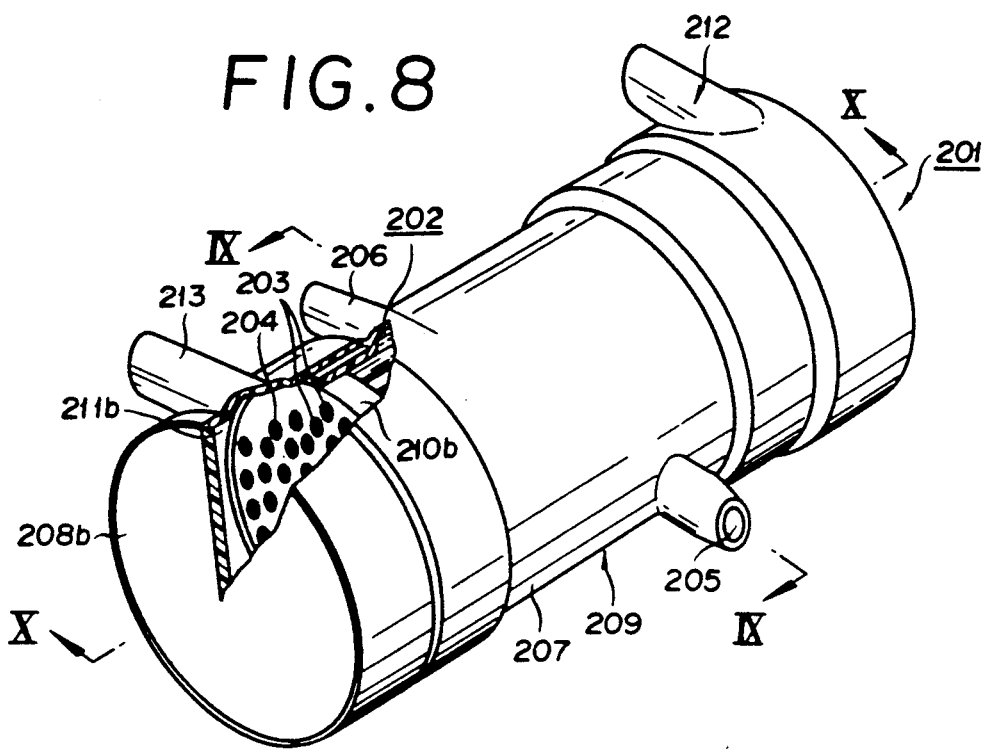
FIG. 8 is a partially cutaway perspective view illustrating the construction of a typical heat exchanger as another embodiment of this invention.
Figure 9:
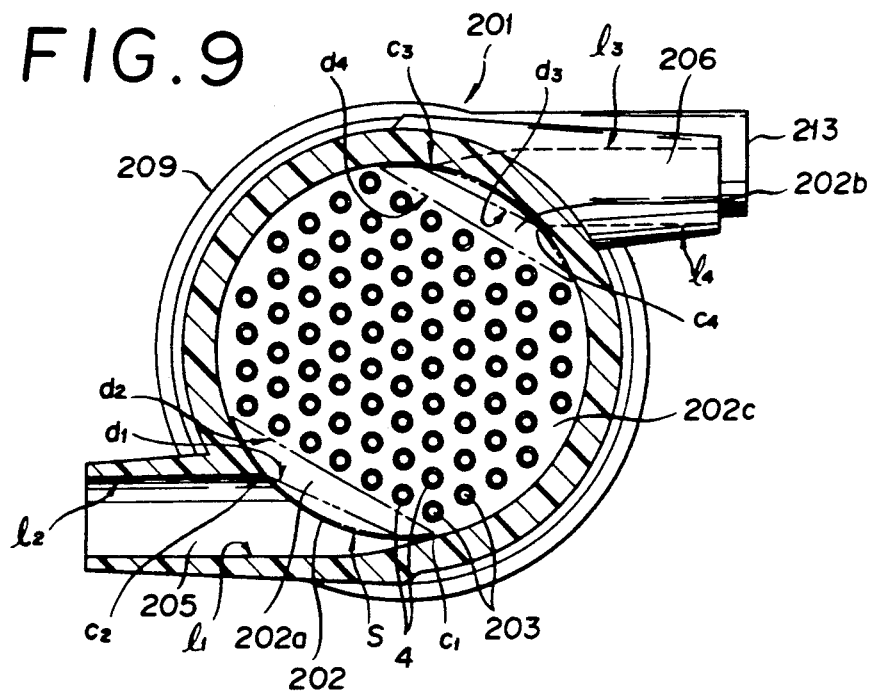
FIG. 9 is a cross section taken through FIG. 8 along the line IX—IX.
Figure 10:
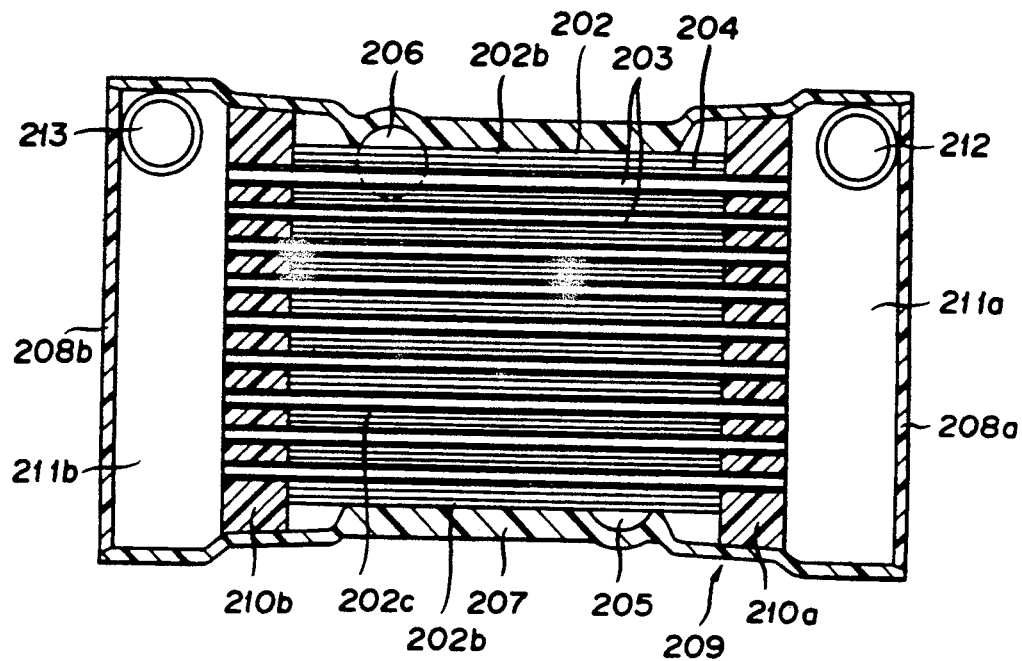
FIG. 10 is a cross section taken through FIG. 8 along the line X—X.

FIGS. 8 to 10 illustrate another embodiment of this invention. This embodiment, similarly to that illustrated in FIGS. 3 to 5, comprises a heat exchanger 201 for medical treatment which comprises a cylindrical blood passing space 202 and a multiplicity of heat-exchanging tubes 204 disposed inside the cylindrical blood passing space 202 along the longitudinal direction of the blood passing space and provided each with an inner space 203 watertightly separated from the blood passing space 202 and effects exchange of heat across the walls of the heat-exchanging tubes 204 between the blood passed through the blood passing space 202 and the heat-exchanging medium passed through the inner spaces 203 of the heat-exchanging tubes 204. This heat exchanger 201 has a salient characteristic thereof the fact that a blood inlet tube 205 for introducing blood into the blood passing space 202 and a blood outlet tube 206 for discharging the blood from the blood passing space 202 are extended inwardly from outside substantially along straight lines perpendicular to the longitudinal direction of the blood passing space 202 and tangent to the peripheral surface of the blood passing space 202 and the heat-exchanging tubes 204 are disposed as uniformly separated mutually throughout the entire blood passing space 202 except for an empty space portion 202a formed by extending in the axial direction of the blood passing space 202 a portion enclosed in the shape of a bow possessing a chord $d_2$ substantially parallel to and equal to or slightly longer than a line segment $d_1$ connecting two points $C_1$, $C_2$ of intersection between two inner peripheral lines $l_1$, $l_2$ of the blood inlet tube 205 and the circumferences of the blood passing space in a cross section perpendicular to the axis of the blood passing space inclusive of the axial line of the blood inlet tube 205 and an empty space portion 202b formed by extending in the axial direction of the blood passing space a portion enclosed in the shape of a bow possessing a chord $d_4$ substantially parallel to and equal to or slightly longer than a line segment $d_3$ connecting two points $C_3$, $C_4$ of intersection between two inner peripheral lines $l_3$, $l_4$ of the blood outlet tube 206 and the circumference S of the blood passing space 202 in a cross section perpendicular to the axis of the blood passing space inclusive of the axial line of the blood outlet tube 206.

When the blood inlet tube 205 and the blood outlet tube 206 are extended inwardly from outside substantially along the straight lines perpendicular to the longitudinal direction of the blood passing space 202 and tangent to the peripheral surface of the blood passing space 202 and allowed to communicate with the blood passing space 202 as described above, the blood introduced through the blood inlet tube 205 is induced to generate a flow tending to revolve inside the blood passing space 202 along the peripheral plance of the blood passing space and the opening through which the blood inlet tube 205 communicates with the blood passing space 202 grows in size. Further, an empty space destitute or devoid of heat-exchanging tubes is present in front of the opening for communication. As the result, the blood introduced through the blood inlet tube 205 flows substantially uniformly throughout the entire blood passing space and comes into uniform contact with substantially all the heat-exchanging tubes 204 disposed within the blood passing space 202 except mainly for the specific group of heat-exchanging tubes 204 located in the central part of the blood passing space 202, namely on the roughly straight line connecting the point of communication with the blood inlet tube 205 and the point of communication with the blood outlet tube 206. By the same token, since the opening for communication of the blood outlet tube 206 with the blood passing space, 202 grows in size and an empty space destitute or devoid of heat-exchanging tubes 204 is present in front of the opening for communication, the blood flowing through any portion within the blood passing space 202 is discharged substatially uniformly out of the blood outlet tube 206. As the result, the exchange of heat within the blood passing space 202 can be carried out uniformly without entailing any locally excessive or insufficient exchange of heat. Further, in the heat exchanger of the present embodiment, since the blood flows outside the heat-exchanging tubes 204 and the opening for communication of the blood inlet tube 205 with the blood passing space 202 grows in size and an empty space destitute of heat-exchanging tubes 204 is present in front of the opening for communication, the blood suffers from no heavy pressure loss during the course of introduction thereof into the blood passing space 202 and entails infliction of only sparing damage upon the blood components.

FIG. 10 is a cross section in the axial direction of the present embodiment.

The heat exchanger for medical treatment of the present embodiment is constructed so that, inside a cylindrical housing 209 comprising a housing proper 207 and end plates 208a, 208b closing the open opposite end parts of the housing proper 207, a multiplicity of heat-exchanging tubes 204 are disposed so as to be mutually separated along the longitudinal direction of the housing 207 and partition walls 210a, 210b disposed in the opposite end parts of the plurality of heat-exchanging tubes 204 retain the heat-exchanging tubes 204 watertightly to the lateral wall of the housing 209 without losing the openings of the heat-exchanging tubes 204. The partition walls 210a, 210b further serve the purpose of partitioning the interior of the housing 209 into three empty spaces. Specifically, the central portion of the housing 209 enclosed with the two partition walls 210a, 210b, the lateral wall of the housing 209, and the outer walls of the heat-exchanging tubes 204 constitutes itself the blood passing space 202 and the two end portions of the housing separated watertightly from the blood passing space 202 and enclosed with the partition walls 210a and the partition walls 210b and the end part walls and the end part walls and the lateral wall of the housing 209 constitute themselves the heat-exchanging medium passing spaces 211a, 211b. These two heat-exchanging medium passing spaces 211a, 211b both communicate with the inner spaces of the heat-exchanging tubes 204 which are watertightly separated from the blood passing space 207. The blood inlet tube 205 and the blood outlet tube 206 communicate with the blood passing space 202 which is constructed as described above. Further, a heat-exchanging medium outlet tube 212 is caused to communicate with the heat-exchanging medium passing space 211a and the heat-exchanging medium inlet tube 213 to communicate with the other heat-exchanging medium passing space 211b.

In the heat exchanger 201 for medical treatment of the present embodiment, the blood inlet tube 205 and the blood outlet tube 206 are extended inwardly from outside substantially along the straight lines perpendicular to the longitudinal direction of the housing and tangent to the peripheral surface of the housing 209, namely extended inwardly from outside substantially along the straight lines perpendicular to the longitudinal direction of the blood passing space 202 and tangent to the peripheral plane of the blood passing space 202, and allowed to communicate with the blood passing space 202. The blood inlet tube 205 and the blood outlet tube 206 extended inwardly from outside need not fall exactly on the straight lines perpendicular to the longitudinal direction of the blood passing space 202 and tangent to the peripheral plane of the blood passing space 202 but may deviate from the straight lines to a slight extent such that they will not be prevented from effectively imparting to the blood passed through the blood passing space 202 a flow along the peripheral plane of the blood passing space 202. Further, the blood inlet tube 205 and the blood outlet tube 206 are required, at least in the portions thereof immediately before their points of communication with the blood passing space 202, to run roughly along the straight lines perpendicular to the longitudinal direction of the blood passing space 202 and tangent to the peripheral plane of the blood passing space 202. For the subsequent portions thereof, the running direction is a matter for arbitrary decision. The positions at which the blood inlet tube 205 and the blood outlet tube 206 are located are not specifically defined. To ensure effective exchange of heat between the heat-exchanging medium passed through the inner spaces of the heat-exchanging tubes 204 inserted inside the blood passing space 202 and the blood passed through the interior of the blood passing space 202, they are required to communicate with the blood passing space 202 at mutually separated positions. Desirably, as illustrated in FIG. 8 and FIG. 10, the blood inlet tube 205 communicates with the blood passing space 202 near either of the partition walls 210a, 210b and the blood outlet tube 206 communicates with the blood passing space 202 near the other partition wall 210b or 210a. Further, the blood inlet tube 205 and the blood outlet tube 206 are desired to assume a positional relation such that they are rotated with an angle of about 180° from each other around the peripheral plane of the blood passing space 202 as illustrated in FIG. 8 and FIG. 9.

Moreover in the heat exchanger 201 for medical treatment of the present embodiment, the heat-exchanging tubes 204 disposed along the longitudinal direction of the blood passing space 202 are distributed so as to be uniformly separated mutually throughout the entire blood passing space 202 except for the empty space portion 202a formed by extending in the axial direction of the blood passing space 202 the portion enclosed in the shape of a bow possessing the chord $d_2$ substantially parallelly to and equal to or slightly longer than the line segment $d_1$ connecting the two points $C_1$, $C_2$ of intersection between the two inner peripheral lines $l_1$, $l_2$ of the blood inlet tube 205 and the circumference S of the blood passing space in the cross section perpendicular to the axis of the blood passing space inclusive of the axial line of the blood inlet tube 205 and the empty space portion 202b formed by extending in the axial direction of the blood passing space 202 the portion enclosed in the shape of a bow possessing a regulating chamber for roughly uniform the flow volume of the blood with respect to the heat-exchanging tubes 204 disposed within the blood passing space 202.

The empty space portion 202a which functions as a blood flow regulating chamber is given a shape formed by extending in the axial direction of the blood passing space 202 the portion enclosed in the shape of a bow possessing the chord $d_2$ substantially parallel to and equal to or slightly longer than the line segment $d_1$ connecting the points $C_1$, $C_2$ of the blood inlet tube 205 and the circumference S of the blood passing space in the cross section perpendicular to the axis of the blood passing space inclusive of the axial line of the blood inlet tube 205 and the empty space portion 202b is similarly given a shape formed by extending in the axial direction of the blood passing space 202 the portion enclosed in the shape of a bow possessing the chord $d_4$ substantially parallel to and equal to or slightly longer than the line segment $d_3$ connecting the two points $C_3$, $C_4$ of intersection between the two inner circumferential lines $l_3$, $l_4$ of the blood outlet tube 206 and the circumference S of the blood passing space 202 in the cross section perpendicular to the axis of the blood passing space inclusive of the axial line of the blood outlet tube 206. These special shapes have been adopted for the following reason. If the empty space portions 202a, 202b are excessively slanted relative to the openings for communication of the blood inlet tube 205 and the blood outlet tube 206 with the blood passing space 202, namely if they are given shapes formed by extending in the axial direction of the blood passing space 202 the portion enclosed in the shape of a bow possessing a chord of a widely different inclination from the line segments $d_1$ and $d_3$, they have the uncomfortable possibility of not only narrowing excessively the empty space portion 202c destined to accommodate the heat-exchanging tubes 204 but also impairing the uniformity of blood flow distribution. Further, if the chords $d_2$ and $d_4$ are much longer than the line segments $d_1$ and $d_3$ (equaling the inside diameters of the openings for communication of the blood inlet tube 205 and the blood outlet tube 206 with the blood passing space 202), they have the unwanted possibility of excessively narrowing the empty space portion 202c destined to accommodate the heat-exchanging tubes. The chords $d_2$, $d_4$ of the bows which are cross sections of the empty space portions 202a, 202b need not be exactly parallel to the line segments $d_1$, $d_3$ but may be different in inclination from the line segments to a slight extent such that they will not be prevented from substantially uniformly distribution the blood flow in the circumferential direction of the blood passing space 202 in front of the openings for communication of the blood inlet tube 205 and the blood outlet tube 206 with the blood passing space 202. For the purpose of forming the empty space portions 202a, 202b effectively, the chords $d_2$, $d_4$ must be at least equal in length to the line segments $d_1$, $d_3$. Although the largest possible lengths of the chords $d_2$, $d_4$ are difficult to define because they variable with their inclination, the arcs of the bows possessing these chords $d_2$, $d_4$ are desired to have a length of not more than ⅜ of the length of the circumference of the blood passing space 202. When the empty space portions 202a, 202b destitute of heat-exchanging tubes 204 are formed within the blood passing space 202, the number of heat-exchanging tubes 204 to be disposed inside the blood passing space 202 naturally decreases proportionately. When the empty space portions 202a, 202b are given the shape described above, the decrease in the number of heat-exchanging tubes brings about substantially no discernible decline of the efficiency of exchange of heat. Further, when two empty space portions 202a, 202b destitute or devoid of heat-exchanging tubes 204 have a total volume of less than 10% of the volume of the blood passing space 202, the decline of the efficiency of exchange of heat is practically nil.

A heat exchanger comprising a cylindrical blood passing space 202 measuring 55.6 mm in radius and 80 mm in length, a blood inlet tube 205 and a blood outlet tube 206 both measuring 12 mm in inside diameter and disposed as described above and allowed to communicate with the blood passing space 202, and a total of 223 heat-exchanging tubes 204 each measuring 2.14 mm in inside diameter and 2.38 mm in outside diameter and distributed as uniformly separated mutually throughout the entire blood passing space 202 except for empty space portions 202a, 202b formed in the aforementioned shape in front of the openings for communication of the blood inlet tube 205 and the blood outlet tube 206 with the blood passing space 202 and occupying a total of 10% of the volume of the blood passing space 202 and another heat exchanger comprising identically, except that the empty space portions 202a, 202b were not formed and heat-exchanging tubes 204 (amounting to 253) were distributed throughout the entire blood passing space 202 including the spaces otherwise occupied by the empty space portions 202a, 202b were produced and actually operated by feeding blood thereto at a rate of 4 liters/minute to test for performance. It was consequently found that the efficiency, $\eta$, of exchange of heat was equally 0.4 for both the heat exchangers and the pressure loss was 1 mm $H_2O$ for the former heat exchanger and 5 mm $H_2O$ for the latter heat exchanger. The results clearly evince the superiority of performance due to the provision of the empty space portions 202a, 202b destitute or devoid of heat-exchanging tubes 204.

The heat exchanger for medical treatment of the present embodiment which is constructed as described above is put to use as suitably incorporated in a varying extracorporeal circulation path. Since it enjoys exceptional compactness and high performance, it can be integrated with an oxygenator and a blood storing tank and used advantageously in the form of an oxygenator system as illustrated in FIG. 6 and FIG. 7, similarly to the heat exchanger of the embodiment of FIG. 3 to FIG. 5.

Figure 11A:
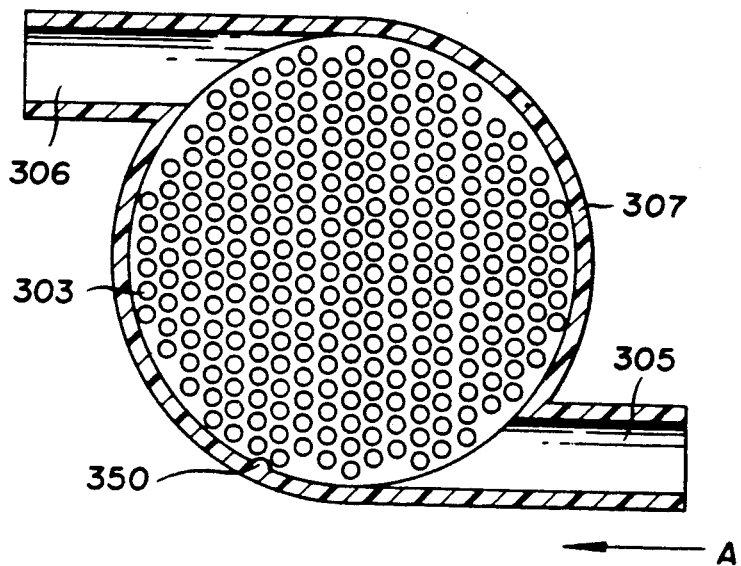
FIGS. 11A and 11B are cross sections of still another embodiments.

FIG. 11A illustrates yet another embodiment of the present invention; specifically a heat exchanger constructed similarly to that of the embodiment illustrated in FIG. 3 to FIG. 5, except that a housing body 307 is provided on the inner wall surface thereof with a rib 350 disposed parallel to a slender tube opposed to the inner wall surface so as to retard the flow of blood between the slender tube 303 and the housing body 307.

Figure 11B:
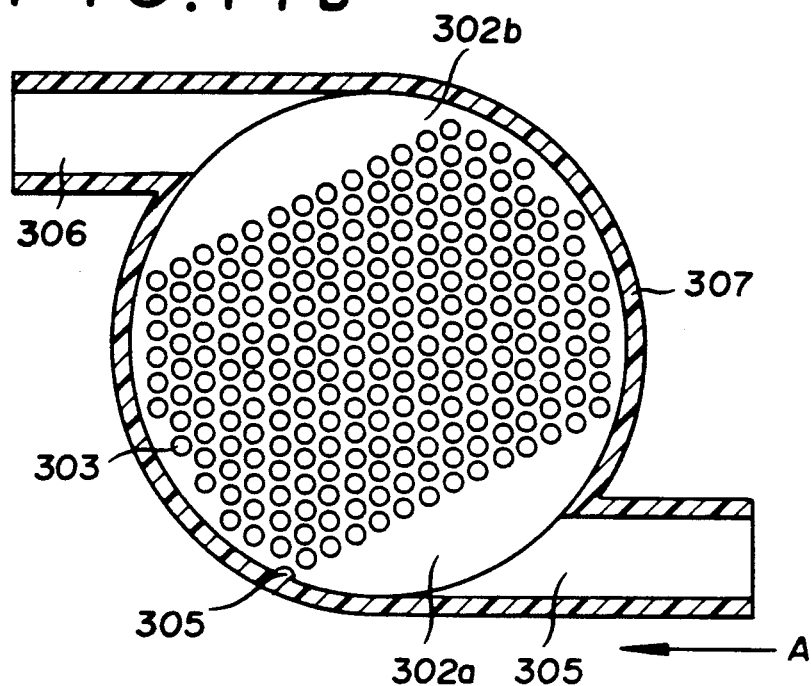

FIG. 11B illustrates still another embodiment of the present invention, specifically a heat exchanger constructed similarly to that of the embodiment illustrated in FIG. 8 and FIG. 9, except that a housing body 307 is provided on the inner wall surface thereof with a rib 350 disposed parallelly to a slender tube 303 opposed to the inner wall surface so as to retard the flow of blood between the slender tube 303 and the housing body 307 and an empty space portion 302a destitute of slender tube 303 is formed near a blood inlet 305 inside the housing body 307. This empty space may not be formed as in the construction of the heat exchanger of FIG.

11A. When this empty space portion is formed, this portion forms a blood chamber part of low inflow resistance and permits a reduction in pressure loss and the blood entering the housing body 307 is allowed to flow into the whole volume of the empty space portion 302a, form a blood flow extending the entire width of the slender tube 303, and then find its way into the bundle of slender tubes 303. The heat exchanger of this embodiment, therefore, is capable of forming a blood flow extending throughout the entire length of the slender tube 303 and effecting exchange of heat with enhanced efficiency.

The heat exchanger is likewise desired to have an empty space portion 302b destitute of slender tube 303 formed near the position at which a blood outlet 306 is located within the housing body 307. This empty space portion 302b forms a blood chamber part, temporarily accommodates the part of blood which has flowed through the interior of the housing body 307, and releases the blood gradually and, as the result, serves the purpose of precluding the possibility that any part of the blood will form a flow which continuously circulates within the housing body 307 and fails to depart from the housing body 307.

In the heat exchangers illustrated in FIG. 11A and FIG. 11B, the rib 350 formed therein as described above is capable of retarding the flow of blood along the inner wall surface of the housing body 307. The rib 350 is desired at least to be extended throughout the entire part of the adjacent slender tube 303 which is exposed to the flowing blood.

Where the slender tubes 303 are accommodated so as to be substantially uniformly separated mutually within the housing body 307, the distance between the rib 350 and the adjacent slender tube 303 is desired to be smaller than the distance between the separated slender tubes. This specific distance permits the flow of blood along the inner wall surface of the housing body 307 to be retarded without fail. More desirably, the rib 350 is in substantial contact with the adjacent slender tube 303. The term "substantial contact" as used herein refers to a distance of not more than 0.2 mm, though variable with the pitch between the separated slender tubes. The rib 350 thus disposed relative to the adjacent slender tube 303 is capable of substantially completely eliminating the flow of blood along the inner wall surface of the housing 302.

Desirably, the rib 350 is disposed near the particular slender tube 303 located in the proximity of the blood inlet 305. The provision of just one rib 350 is sufficient for the purpose mentioned above. The heat exchanger may be provided with a plurality of such ribs 350 on condition that they are so shaped and positioned as to avoid retention of bubbles. Particularly where the blood inlet 305 is so attached as to be directed toward the inner surface side of the housing body 307 at a stated angle from the center of the housing body 307 as illustrated in FIG. 11A and FIG. 11B, since the flow of blood along the inner wall surface of the housing substantially advances in the direction of the blood inlet 305 (the direction indicated by the arrow A), at least one rib 350 disposed on the inner wall surface of the housing toward which the blood inflow 305 is directed is sufficiently capable of retarding the greater part of the flow of blood along the inner wall surface of the housing.

The heat exchanger of the present embodiment has been so far described as having a housing body 307 provided with a heat-exchanging medium inlet and a heat-exchanging medium outlet. This embodiment need not be limited to this construction. The heat exchanger may be modified by disposing partition walls one each in the opposite end parts of the housing body and attaching to the outer surface of one of the partition walls a cap-shaped medium inlet side port provided with heat-exchanging medium inlets communicating with the inner spaces of the slender heat-exchanging tubes and to the outer surface of the other partition wall a cap-shaped medium outlet side port provided with a heat-exchanging medium outlet. The attachment of these ports may be attained by the use of a clamping ring or by means of fusion with ultrasonic waves or high-frequency waves or adhesion with an adhesive agent, for example.

Figure 12:
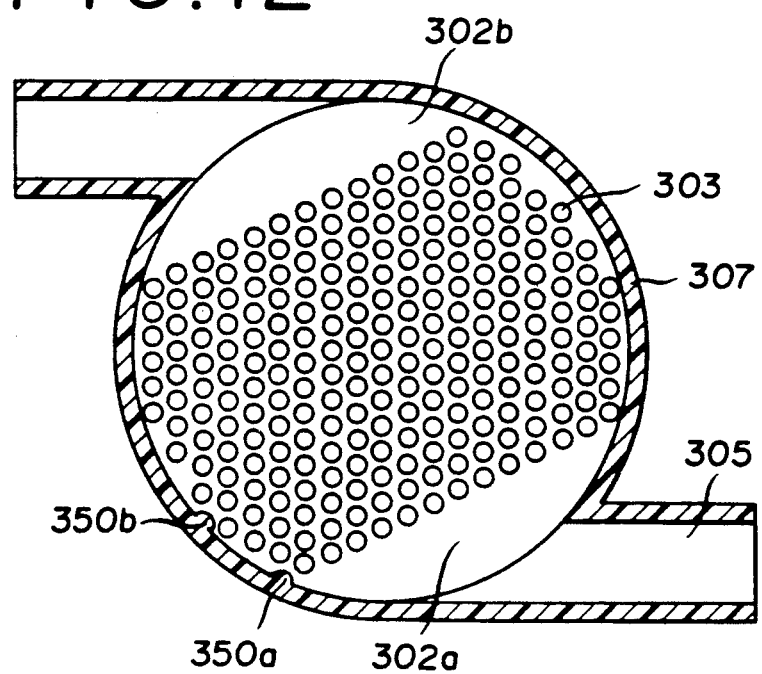
FIG. 12 is a cross section of yet another embodiment.

While the use of just one rib is sufficient at times, use of two ribs 350a, 350b illustrated in FIG. 12 or use of more ribs proves to be desirable at other times.

Now, a heat exchanger for blood as a still further embodiment of this invention will be described below with reference to FIG. 13.

The difference between the embodiment illustrated in FIG. 13 and that illustrated in FIG. 11A and FIG. 11B consists in the shape of the housing body 307. In FIG. 13, therefore, the parts which have equivalents in FIG. 11A and FIG. 11B will be denoted by the like reference numerals plus 100.

A housing body 407 is formed in the shape of a polygonal cylinder.

In the embodiment illustrated in FIG. 13, a blood inlet 405 is attached in a direction parallel to one of the surfaces of the polygonal housing body 407. To be more specific, it is so attached as to protrude perpendicularly from the end part of one of the planes of the polygonal housing body 407. A blood outlet 406 is similarly attached in a direction parallel to one of the surfaces of the polygonal housing body 407. To be more specific, it is so attached as to protrude perpendicularly from the end part of one of the surfaces of the polygonal housing body 407. Desirably, the blood outlet 406 is disposed in a direction substantially parallel and opposite to the blood inlet 405. The heat exchanger is provided with an empty space portion 402a destitute of slender tubes 403 near the position at which the blood inlet is located in the housing body 407 to ensure effective introduction of blood in spite of the attachment of a blood circuit or an oxygenator to the blood outlet. The empty space portion 402a thus provided in the housing body 407 temporarily accommodates the blood entering the housing and prevents the blood from directly advancing into the bundle of slender tubes. The blood which has filled this empty space portion 402a is then allowed to rise upwardly and then flow inside the housing body 407.

The heat exchanger is further provided with an empty space portion 402b destitute of slender tubes 403 near the position at which the blood outlet 406 is located inside the housing body 407. The empty space portion 402b thus provided in the housing body 407 temporarily accommodates a multiplicity of blood flows passed through the inner spaces of the bundle of slender tubes and combines them into one blood flow destined to advance toward the blood inlet 406. Owing to this function of the empty space poriton 402b, the multiplicity of blood flows about to rise through the inner spaces of the bundle of slender tubes are allowed to continue their advance through the bundle of slender tubes without being affected by an external force tending to speed up or slow down the flow.

The slender tubes 403 are arranged within the housing body 407 in rows parallel to the direction of the blood inlet as illustrated in FIG. 13. The individual rows of slender tubes are so disposed that the individual slender tubes in the adjacent rows are staggered. In this arrangement, therefore, the blood flows rising from below find their way through the spaces intervening between the individual slender tubes in the lower row, collide against the individual slender tubes of the immediately upper row, then find their way through the spaces intervening between the same individual slender tubes, and continue their ascent by repeating these motions through the rest of the rows of slender tubes. The rows thus formed of the slender tubes 403 may be slanted at a stated angle from the direction of the blood inlet instead of being perfectly parallel thereto.

The housing body 407 is provided on the inner wall surface thereof with a rib 450 which is extended in the axial direction of the housing body 407 parallel to a particular slender tube 403 opposed to the portion of the inner wall surface of the housing destined to seat the rib, so as to retard the flow of blood between the adjacent slender tube 403 an the inner wall surface of the housing body 407. The rib 450 disposed as described above in the housing body 407 is capable of dispersing the flow of blood along the inner wall surface of the housing body 407. The rib 450 is desired at least to be extended throughout the entire part of the adjacent slender tube 403 which is exposed to contact with the blood.

Where the slender tubes 403 are accommodated so as to be substantially uniformly separated mutually within the housing body 407, the distance between the rib 450 and the adjacent slender tube 403 is desired to be smaller than the distnace between the separated slender tubes. This specific distance permits the flow of blood along the inner wall surface of the housing body 407 to be retarded without fail. More desirably, the rib 450 is in substantial contact with the adjacent slender tube 403. The term "substantial contact" as used herein refers to a distance of not more than 0.2 mm, though variable with the pitch between the separated slender tubes. The rib 450 thus disposed relative to the adjacent slender tube 403 is capable of substantially completely eliminating the flow of blood along the inner wall surface of the housing 402.

Desirably, this rib 450 is disposed near the particular slender tube 403 which is located near the blood inlet 405. Further in the present embodiment, the blood which has filled the empty space portion is allowed to ascend and continue its flow inside the housing. Similarly to the embodiment illustrated in FIG. 6, the blood flows more readily between the inner wall surface of the housing body 407 and the slender tubes opposed to the inner wall surface than through the spaces between the individual slender tubes in the present embodiment. Further in the present embodiment, since no appreciable difference occurs in the flow rate of blood between the opposed surfaces of the polygonal housing body, ribs may be formed one each on the opposed inner surfaces of the housing.

The opposite end parts of the slender tube 403 are watertightly fixed to the housing body 407 with partition walls similarly to those in the embodiment of FIG. 6. A heat-exchanging medium inlet is formed near the end part of the housing beyond one of the partition walls and a heat-exchanging medium outlet near the end part of the housing beyond the other partition wall. The heat-exchanging medium inlet and the outlet both communicate with the inner spaces of the slender heat-exchanging tubes. A seal member is fitted in one end part of the housing. Another seal member is similarly fitted in the other end part of the housing.

The housing, instead of being provided with the heat-exchanging medium inlet and the heat-exchanging medium outlet, may be provided with partition walls disposed one each in the end parts of the housing, a cap-shaped medium inlet side port possessed of a heat-exchanging medium inlet communicating with the inner spaces of the slender heat-exchanging tubes and formed in the outer surface of one of the partition walls, and cap-shaped medium outlet side port possessed of a heat-exchanging medium outlet and formed in the outer surface of the other partition wall. The fixation of these ports may be effected by the use of clamping rings or by means of fusion with ultrasonic waves or high-frequency waves or adhesion with an adhesive agent.

As slender-heat-exchanging tubes, the heat exchanger of the present invention is desired to be provided in the housing thereof with about 10 to 2,000, preferably about 50 to 1,000, metallic tubes of high thermal conductivity (such as, for example, stainless steel tubes, aluminum tubes, or copper tubes) having an inside diameter in the range of 0.5 to 10 mm, preferably 2 to 5 mm. These slender tubes are accommodated in the housing parallel to the axial direction of the housing. The blood introduced through the blood inlet, therefore, flows inside the housing in such a direction as to traverse the slender tubes. The slender tubes are separated by a fixed distance. This distance, though variable with the outside diameter of slender tube or the inside diameter of housing, for example, generally falls approximately in the range of 0.2 to 4 mm, preferably 0.8 to 2 mm.

The housing is made of any of various materials such as polycarbonate, acryl-styrene copolymer, and acryl-butylene-styrene copolymer. The seal members used for sealing the opposite ends of the housing are discs possessed of an outer contour substantially equal to the inner contour of the end parts of the housing and made of any of various materials such as polycarbonate, acryl-styrene copolymer, and acryl-butylene-styrene copolymer. These seal members are fixed watertightly to the end part of the housing by means of adhesion with adhesive agent or solvent or fusion with high-frequency waves, ultrasonic waves, or induction heating.

Figure 14:
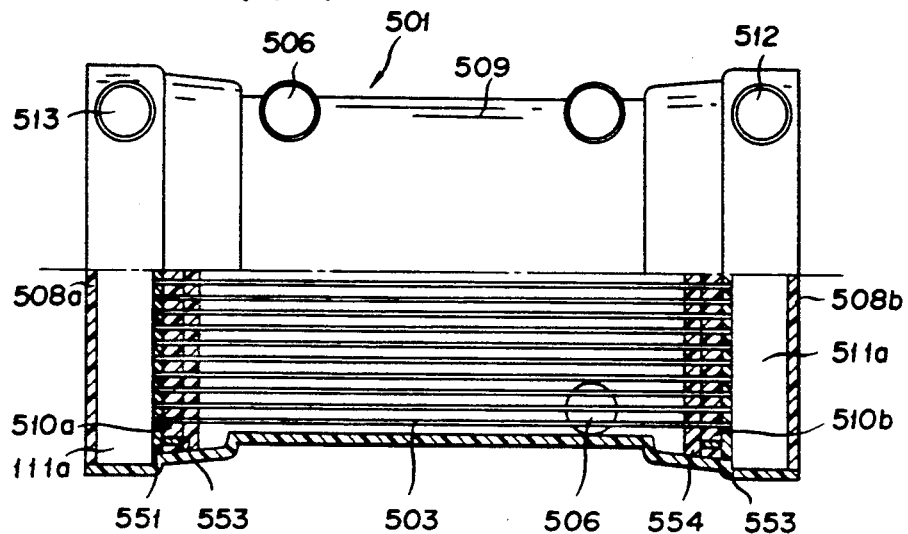
FIG. 14 is a partially cutaway front view illustrating the another embodiment of the heat exchanger of the present invention.
Figure 15:
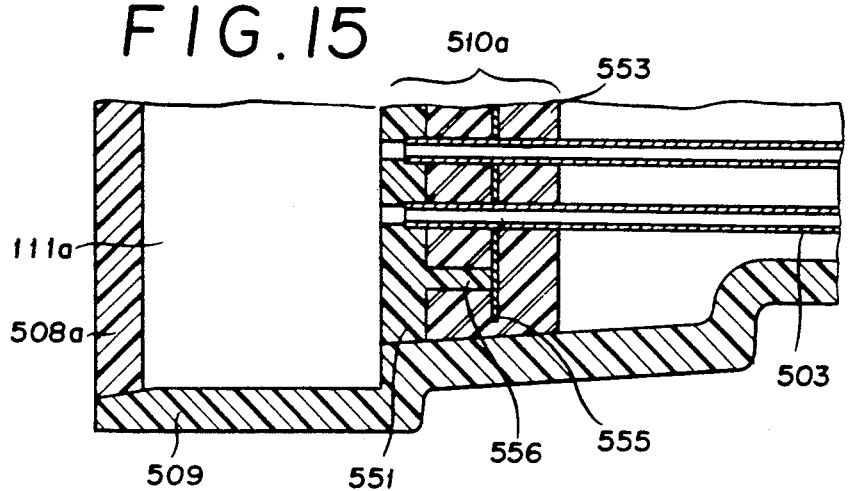
FIG. 15 is a partially enlarged cross section of FIG. 14.

FIG. 14 and FIG. 15 illustrate a further embodiment of the present invention. The difference between the heat exchanger of this embodiment and that of the embodiment illustrated in FIG. 3 to FIG. 5 consists mainly in the construction of partition walls 510a, 510b. In FIG. 14 and FIG. 15, the parts which have equivalents in FIG. 3 to FIG. 5 are denoted by like reference numerals plus 400. FIG. 15 is a magnified cross section illustrating a partition wall and adjacent parts of the heat exchanger of FIG. 14.

A cylindrical housing 509 of a heat exchanger 501 accommodate therein a multiplicity of slender heat-exchanging tubes 503. The housing 509 and the slender tubes 503 are equal to those already described. In the present embodiment, partition walls 510a, 510b are formed respectively of perforated plates 551, 552 and potting compounds 553, 554. The partition walls will be described specifically with reference to FIG. 15. The perforated plate 551 possesses a multiplicity of holes each having an inside diameter larger than the outside diameter of slender tube 503 at one end thereof and an inside diameter smaller than the outside diameter of slender tube 503 at the other end thereof. In the embodiment of FIG. 15, the perforated plate 551 possesses holes which have an inside diameter converged from one end to the other thereof so as to decrease past the outside diameter of the slender tubes 503 halfway along the wall thickness of the perforated plate. The end parts of the slender tubes 503 are inserted into these holes in the perforated plate. Further, the perforated plate 551 is provided with a plurality of (at least two) ribs 556 serving the purpose of keeping a slender tube dispersing plate 555 apart from the perforated plate 551. The slender tube dispersing plate 555 is intended to impart a fixed pattern to the bundle of slender tubes 503 in a dispersed state and, therefore, is provided with a multiplicity of holes fit for insertion of the slender tubes 503. The provision of the slender tube dispersion plate and the ribs, though not an indispensable requirement, proves to be desirable in the sense that it ensures uniform dispersion of the slender tubes 503. The potting compound 553 fixes the slender tubes 503 watertightly to the perforated plate 551 and the perforated plate 551 similarly watertightly to the housing 509. The slender tube dispersing plate 555 is completely buried in the potting compound. The complete embedment in the potting compound brings about an advantageous effect in preventing the blood under treatment from coming into direct contact with the dispersing plate. The partition walls 510b and the adjacent parts are similarly constructed.

Figure 16:
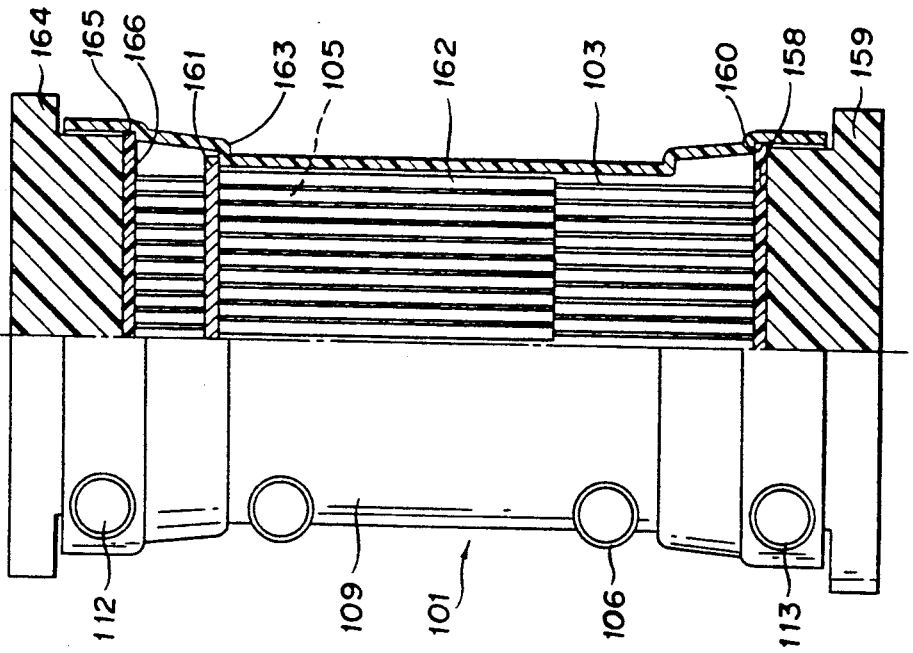
FIG. 16 is a drawing for explaining the manufacturing process of the heat exchanger in accordance with the present invention.
Figure 1:
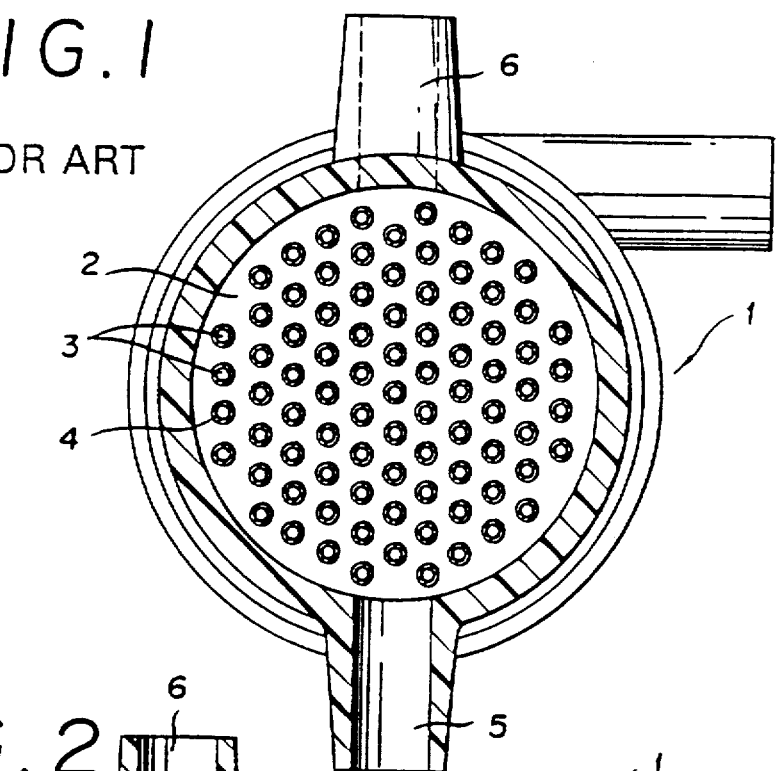
Figure 2:
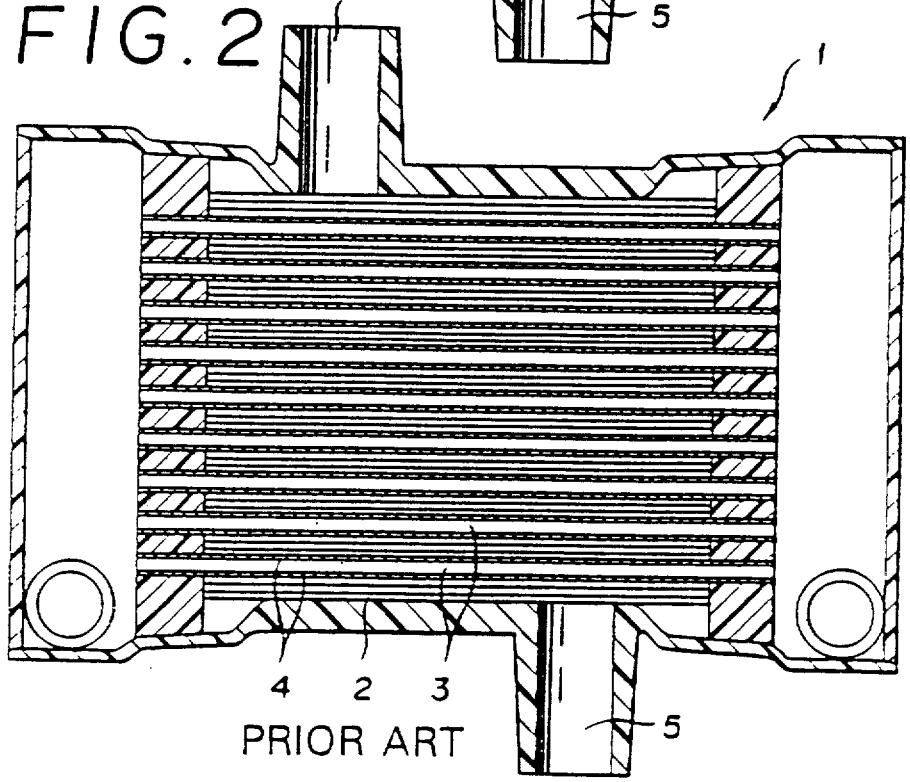

Now, the method employed for the production of the heat exchanger for medical tretment of the present invention illustrated in FIG. 3 to FIG. 5 will be described below with reference FIG. 16. FIG. 16 is a process diagram illustrating the flow of the steps in the method for the production of the heat exchanger of this invention.

The method for the production contemplated by the invention comprises the steps of forming a cylindrical housing possessing heat-exchanging medium ports 112, 113 disposed one each at the opposite end parts thereof and a blood inlet port 105 and a blood outlet port 106 disposed at positions between the medium ports 112, 113, attaching a first sealing member at a position between the medium port (medium inlet port 113, for example) and the blood port (blood outlet port 106, for example) located at one end part of the cylindrical housing 109, inserting through the other end part of the cylindrical housing 109 into the cylindrical housing a slender tube distributing device (i.e., arranging member 157) possessing a multiplicity of holes fit for insertion of slender heat-exchanging tubes and a multiplicity of slender heat-exchanging tubes 103, attaching a second sealing member at a position between the medium port (medium outlet port 113, for example) and the blood port (blood inlet port 105 or blood outlet port 106, for example) which are located at the other end part of the cylindrical housing 109, injecting a potting compound through the blood port (blood outlet port 106, for example) on one end part side and the blood port (blood inlet port 105 or blood outlet port 106, for example) on the other end part side of the cylindrical housing 109 with the end parts of the slender heat-exchanging tubes kept in a closed state, thereby forming partition walls 110a, 110b for fixing the opposite end parts of the slender heat-exchanging tubes 103 to the cylindrical housing 109, removing the first sealing member and the second sealing member, and fitting seal membrs 508a, 508b one each to the opposite ends of the cylindrical housing 109. To be more specific, after the housing 109 has been formed, one end part of the housing 109 is closed fast by having the sealing member fitted to the end part of the housing 109 at a position (falling between the medium inlet port 113 and the blood outlet port 106, for example) approximating the medium port. The first sealing member is intended to close the end parts of the slender heat-exchanging tubes 103 when the second sealing member is depressed into place as described later on. The sealing members are desired to be formed of an elastic sealing member 158 (a rubber sheet of silicone rubber, polyurethane rubber, or latex rubber, for example) possessing a cross-sectional contour matched to that of the housing 109 as held in the aforementioned place and a retaining device (i.e., first provisionally closing member) 159 serving to keep the elastic sealing member in place. The elastic sealing member 158 must be incapable of adhering to the potting compound which is poured into the housing 109 later. This requirement may be met by using the potting compound and the elastic sealing member which are made of materials devoid of adhesion quality (silicone rubber sheet for the elastic sealing member and polyurethane as the potting compound or silicone rubber as the potting compound and polyurethane for the elastic sealing member, for example) or, where the materials therefor both possess adhesive quality, by coating the surface of the elastic sealing member 158 falling on the inner surface side of the housing 109 with resin of the kind capable of cancelling the adhesive quality of the materials (such oil as silicone oil for example). The end parts of the housing 109, as illustrated in FIG. 5 and FIG. 16, are radially diverged in the direction of their extremities from the positions approximating the heat exchanging medium ports 112, 113. The end part of the housing 109 is closed by having the elastic sealing member 158 fitted into the radially diverged portion 160. The possible separation of the elastic sealing member 158 from the housing is precluded by the retaining device 159.

Figure 17:
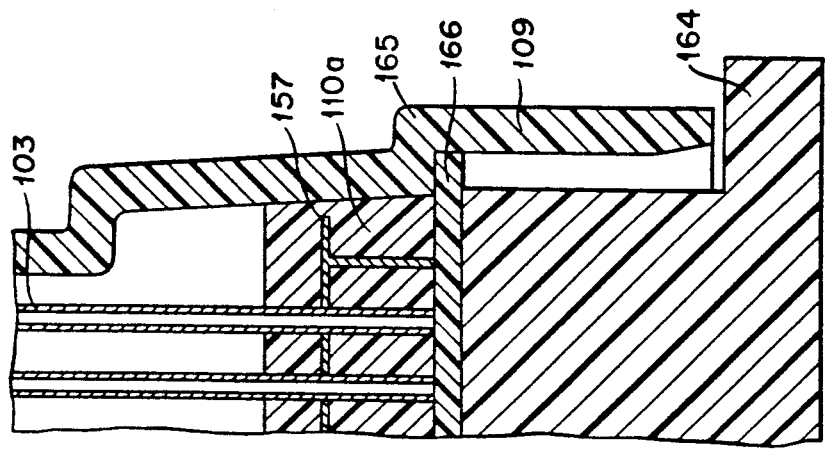
FIG. 17 is a partial enlarged cross section of FIG. 16.

Subsequently, the housing 109 is stood upright on the side thereof provided with the aforementioned retaining device 159 and the slender tube-dispersing device 157 is inserted in the housing 109. The slender tube-dispersing device is intended to impart a state pattern to the bundle of slender tubes 103 to be held in a mutually separated state and, therefore, provided with a multiplicity of holes for insertion of the slender tubes 103. In the embodiment illustrated in FIGS. 15, 16 and 17 the slender tube-dispersing device 157 comprises a plate 161 possessing multiplicity of holes matched to the slender tubes 103 in a bundled state and a multiplicity of pipes 162 having the end parts thereof inserted in the holes of the plate 161. The pipes 162 are fixed in the plate 161. The pipes 162 have an inside diameter so larger than the inside diameter of the slender tubes 103 that the slender tubes 103 can be inserted into the pipes 161. The largest part of the plate 162 has an outside diameter larger than the inside diameter of the middle part of the housing 109 and smaller than the radially diverged portion 163 so that when this plate is inserted into the housing 109, it will be hung down from the radially diverged portion 163 as illustrated in FIGS. 16 and 17. The pipes 162 have a length so adjusted that they will not reach the blood outlet port 106 located below when the slender tube-dispersing device 157 is inserted into the housing 109 (namely hung down from the radially diverged portion 163 with the plate 161). This adjustment of length is necessary for the purpose of preventing the pipes 162 of the slender tube-dispersing device 157 from being fixed with the potting compound which will be poured in through the blood outlet port 106 later on. The slender tube-dispersing device using the pipes in the manner described above permits the bundle of slender tubes to be dispersed certainly in a pattern aimed at. Further, owing to the use of such pipes as mentioned above, the slender tubes 103 and the slender tube-dispersing device 157 contact each other in large portions enough for the slender tubes to be steadily retained in a dispersed state and to be prevented from otherwise possible disruption of the dispersed state under the impact of the potting compound during the injection of the potting compound. After the insertion of the slender tube-dispersing device 157, the slender tubes 103 are inserted into the pipes 162 which has been already inserted through the holes of the plate 164 of the dispersing device 157. The slender tubes 103 thus inserted have the lower end parts thereof thrust out of the leading ends of the pipes 162. The leading ends of the slender tubes 103 come into contact with the elastic sealing member 158. The slender tubes 103 have a length so adjusted that the upper ends thereof fall in the neighborhood of the radially diverged portion of the housing 109. Then, the second sealing member is fitted downwardly into the radially diverged portion 165 of the housing 109 to seal the other end part of the housing 109. The second sealing member, similarly to the first sealing member, is desired to comprise an elastic sealing member 166 possessing a cross-sectional contour matched to that of the housing 109 held in the place mentioned above and a retaining device 161 adapted to keep the elastic sealing member 166 in place. This sealing member is advantageously made of the same material as mentioned above. When the retaining device 164 is depressed into place from above, the end parts of the slender tubes 103 are closed with the elastic sealing members 158, 166. The heat exchanger has been so far described as being provided with the elastic sealing member 166. Since it is only required to close the end parts of the slender heat-exchanging tubes, the installation thereof is not necessarily indispensable up to this point in the whole course of the production. Then, the potting compound is poured in through the blood outlet port 106 are allowed to set. Subsequently, the upper retaining device 164, the elastic sealing member 166, and the slender tube-dispersing device 157 are removed. Further, the elastic sealing member 166 is fitted in the radially diverged portion 165 of the housing 109 to close the other end of the housing 109 and set in place with the retaining device 162. Now, the housing 109 is turned upside down and the retaining device 164 is depressed into place from above to close the end parts of the slender tubes 103. In the same manner as described above, the potting compound is poured in through the blood outlet port (or the blood inlet port 105) and allowed to set. After the potting compound has been solidified, the retaining devices 159, 164 and the elastic sealing members 158, 166 attached to the opposite end parts of the housing 109 are removed. Consequently, the partition walls 110a, 110b are formed.

Since the method described above requires the removal of the slender tube-dispersing device as one of the essential steps thereof, the injection of the potting compound can be attained infallibly and easily even on the side used for the insertion of the slender tube-dispersing device 157. Since the opposite ends of he slender tubes 103 are kept in place with the elastic sealing members 158, 166, the elastic sealing members absorb any possible minor variation of length of the slender tubes 103 and are capable of preventing the potting compound from flowing into the slender tubes 103. Further, the seal members 108a, 108b possessing a cross-sectional contour matched to that of the opposite ends of the housing 109 are fixed watertightly to the opposite end parts of the housing 109. The fixation of the seal members is attained by adhesion with an adhesive agent or by fusion with high-frequency waves, ultrasonic waves, or induction heating.

The heat exchanger has been so far described as being provided with sealing members comprising elastic sealing members 158, 166 and retaining devices 159, 164. Optionally, the sealing members used for the heat exchanger may be of the type produced by integrally forming the elastic sealing members and the retaining devices.

The insertion into the cylindrical housing 109 through the other end part of the cylindrical housing 109 of the slender tube-dispersing device possessing a multiplicity of holes of insertion of slender heat-exchanging tubes and the multiplicity of slender heat-exchanging tubes may be carried out with the housing kept in a horizontal state. The insertion carried out with the housing kept in an upright state proves to be more desirable because the slender tubes can be inserted with greater ease. The insertion into the cylindrical housing 109 through the other end part of the cylindrical housing 109 of the slender tube-dispersing device possessing a multiplicity of holes for insertion of slender heat-exchanging tubes and the multiplicity of slender heat-exchanging tubes may be effected, for example, by first inserting the slender tubes 103 through the holes of the slender tube-dispersing device 157 and then causing the slender tube-dispersing device 157 now holding the slender tubes 103 inserted therethrough to be inserted in the housing 109. The formation of the partition walls may be carried out, for example, by rotating the housing 109 about the axis thereof while keeping the end parts of the slender heat-exchanging tubes 103 fast in place, then centrifugally pouring the potting compound through the blood port on one end part side of the cylindrical housing 109, allowing the introduced potting compound to set, and repeating the same procedure on the other end side. Otherwise, it may be effected by rotating the housing about the central part of the housing and, at the same time, centrifugally pouring the potting compound simultaneously through the blood ports on the opposite end parts and allowing the introduced potting compound to set.

The step of fitting the seal members 508a, 508b, to the opposite ends of the housing 109 may comprise first removing either the first sealing member or the second sealing member, fitting one of the seal members to the end part on the side on which the removal just mentioned has been made, removing the remaining sealing member, and fitting the other seal member to the end part on the side on which the removal has been made.

The method for production has been so far described as requiring the removal of the slender tube-dispersing device as one of the component steps. When the slender tube-dispersing device 157 is such that the continued presence thereof within the housing offers no hindrance whatever to the use of the heat exchanger, it need not be removed by all means. As a concrete example of the slender tube-dispersing device 157 which answers the description, a plate formed of a metallic substance such as stainless steel or a synthetic resin as illustrated in FIGS. 16 and 17 may be cited. This slender tube-dispersing device 157 is provided with a plate part possessing a multiplicity of holes permitting insertion thereof of the slender tubes 103 and a plurality (at least three) of leg parts extended downwardly from the plate part. The plate part has a lateral part thereof out away to permit downward flow of the potting compound. When the slender tube-dispersing device of this construction is used in pouring the potting compound through the blood port, it is eventually buried in the partition wall to be formed of the potting compound. Thus, this slender tube-dispersing device places no hindrance whatever in the way of actual use of the heat exchanger.

FIG. 18 is a partially cutaway perspective view illustrating typical heat exchanger for medical treatment as still another embodiment of this invention. As clearly noted from the partition wall, a heat exchanger 601 of this embodiment similar to the heat exchanger of the embodiment illustrated in FIG. 3 to FIG. 5 is provided in one heat-exchanging medium passing space 611b with a heat-exchanging medium outlet port 612 and in the other heat-exchanging medium passing space 611b with a heat-exchanging medium inlet port 613.

In the heat exchanger 601 of the present embodiment, the heat-exchanging medium outlet port 612 and the heat-exchanging medium inlet port 613 are not formed integrally with a housing 609 but are formed by being extended from the outer all surfaces of the housing 609 with flexible tubes 614, 615. The flexible tubes 614, 615 are only required to exhibit substantial and ample flexibility and permit suitable change of positions of the heat-exchanging medium outlet port 612 and the heat-exchanging medium inlet port 613 attached to the leading ends of the flexible tubes 614, 615 and, further, desirably to enable the flexible tubes themselves to be effectively pinched with clamps. They are not discriminated particularly by such factors as material, length, and wall thickness.

Further in the embodiment illustrated in FIG. 18, the second fluid which flows in the closed space of the housing is a heat-exchanging medium. To be specific, this heat exchanger is so constructed that the heat-exchanging medium is passed outside the heat-exchanging tubes 604. The heat exchanger for medical treatment in the present embodiment may be alternatively constructed so that the heat-exchanging medium will flow through the inner spaces of the heat-exchanging tubes 604 (namely the first fluid passing through the inner spaces of the heat-exchanging tubes will be the heat-exchanging medium).

The heat exchanger 601 for medical treatment of the present embodiment which is constructed as described above possesses a highly desirable operating property and is used advantageously as incorporated in a varying kind of extracorporeal circulation path. For example, it can be used advantageously as integrated with an oxygenator and a blood storing tank as illustrated in FIG. 6 and FIG. 7 and allowed to function as an oxygenator system.

In the oxygenator system to be formed by integrating the heat exchanger for medical treatment with the blood storing tank and the oxygenator as described above, the blood withdrawn from the patient's body first flows into the heat exchanger 601 through the blood inlet tube 605. In the meantime, the water introduced as a heat-exchanging medium through the heat-exchanging medium inlet port 613 connected by means of a coupler, for example, to a connection tube (not shown) led out of the heat-exchanging medium temperature controller is passed into the heat-exchanging medium passing space 611a, forwarded through the inner spaces 603 of the heat-exchanging tubes 604, brought to the heat-exchanging medium passing space 611b, discharged from the heat-exchanging medium outlet port 612 into another connection tube (not shown) led out of the heat-exchanging medium temperature controller, and returned to the heat-exchanging medium temperature controller. The exchange of heat across the walls of the heat-exchanging tubes 604 within the blood passing space 602 of this heat exchanger 601 for medical treatment is effected efficiently and uniformly. The blood which has been heated or cooled to a desired temperature in consequence of the exchange of heat is led out of the heat exchanger 601 through the blood outlet tube 606 and then forwarded to the oxygenator 121 through the blood inlet tube 131 of the oxygenator 121 communicating watertightly with the blood outlet tube 606. The blood introduced through the blood inlet tube 131 of the oxygenator 121, while passing through the blood chamber 130, exchanges gas with the oxygen-containing gas flowing through the inner spaces of the hollow fiber membranes 124 thruogh the medium of the hollow fiber membranes 124. As the result, the blood is divested of excessive carbon dioxide gas and replenished with fresh oxygen. The blood which has been oxygenated flows out of the blood outlet tube 132 of the oxygenator 121 and advances into the blood storing tank 141 through the blood inlet 142 of the blood storing tank 141. The blood which has flowed from the blood inlet 142 to the communicating blood inlet part 143 and then reached the defoaming member 147 disposed en route to the blood inlet part 143 is defoamed during the passage thereof through the defoaming member 147 by the fact that the multiplicity of bubbles contained in the blood come into the foam cells of the defoaming member 147, grow by agglomeration, and pass from within the blood into the upper empty space within the blood storing tank 141. The defoamed blood moves on to the communicating blood storing part 144, remains temporarily in the blood storing part 144, departs from the blood outlet 145 disposed below the blood storing part 144, and returns to the patient's body. In the heat exchanger 601 for medical treatment in the present embodiment, the heat-exchanging medium inlet port 613 and the heat-exchanging medium outlet port 612 are disposed as extended with the flexible tubes 614, 615 from the outer wall surfaces of the housing 609 as described above. If a variation occurs in the positional relation between the heat exchanger 601 for medical treatment and the heat-exchanging medium temperature controller during the course of the extracorporeal circulation, it can be completely absorbed by the freedom of twist enjoyed by the flexible tubes 614, 615. Thus, the possibility of their connection being dissolved during the course of the operation mentioned above is nil.

After the extracorporeal circulation treatment is completed, the blood remaining in the oxygenator system must be recovered. This recovery is easily obtained by clamping the flexible tubes 614, 615 of the heat exchanger 601 for medical treatment because the oxygenator system is now ready to be titled freely without entailing the otherwise possible leakage of the heat-exchanging medium.

EXAMPLE 1

A cylindrical housing was used which was formed of polycarbonate in the shape (72 mm in inside diameter, 79 mm in outside diameter, and 150 mm in length) illustrated in FIG. 3 and FIG. 11B, with a blood inlet 105 disposed on the lower part of the housing and two blood outlets on the upper part of the housing, the blood inlet and the blood outlets attached to the housing in directions substantially tangent to the outer surface of the housing, and heat-exchanging medium inlet and outlet disposed near the end parts of the housing.

As slender heat-exchanging tubes, 223 of stainless steel tubes (2.14 mm in inside diameter) were accommodated inside the housing as mutually separated by a distance of 0.82 mm. Inside the housing, empty space portions destitute of slender tube were formed one each near the positions at which the blood inlet and the blood outlets were located.

On the inner wall surface of the housing, one rib 350a of the shape illustrated in FIG. 12 was disposed as extended in the axial direction of the housing parallelly to the particular slender tube opposed to the inner wall surface of the housing seating the rib. This rib measured 3 mm in width and 1.5 mm in height. The distance between the rib and the adjacent tube was 0.4 mm. Since the housing was radially diverged toward the end parts thereof, this distance was found as an average of distances measured in the end parts and in the central part. The slender tubes were fixed to the housing by using polyurethane as a potting compound. A heat exchanger contemplated by this invention was completed by closing the opposite end parts with seal members.

EXAMPLE 2

A heat exchanger was produced by following the procedure of Example 1, except that a housing was formed of polycarbonate in the shape illustrated in FIG. 3 and FIG. 11A and one rib 350 was disposed on the inner wall surface of the housing.

EXAMPLE 3

A heat exchanger was produced by following the procedure of Example 1, except that a rib was disposed at the position indicated 350b in FIG. 13.

EXAMPLE 4

A heat exchanger was produced by following the procedure of Example 1, except that no rib was formed on the inner wall surface of the housing.

EXAMPLE 5

A heat exchanger was produced by following the procedure of Example 2, except that no rib was formed on the inner wall surface of the housing.

EXAMPLE 6

The heat exchangers obtained in Examples 1 to 5 were each subjected to the following test. In the test, water was used in the place of blood and water was also used as a heat-exchanging medium.

To a given heat exchanger, water at a temperature of 40° C. was introduced through the heat-exchanging medium inlet at a rate of 15 liters/min and water at a temperature of 30° C. was introduced through the blood inlet at a varying rate of 2 liters, 4 liters, or 6 liters per minute. The temperature of the water at the blood inlet (TBo) and the temperatue of the water at the medium inlet (TWo) were measured.

The efficiency of exchange of heat ($\eta$) was calculated from the following formula using the results of measurement:

$$\eta = (TBo - TBi)/(Twi - TBi)$$

wherein TBi stands for the temperature of the water flowing in through the blood inlet, and TWi for the temperature of the water flowing in through the heat-exchanging medium inlet. The results of the test are shown in Table 1.

TABLE 1

| Flow volume (liters) | Efficiency of exchange of heat ($\eta$) Example | | | | |
|---|---|---|---|---|---|
| | 1 | 2 | 3 | 4 | 5 |
| 2 | 0.76 | 0.75 | 0.74 | 0.64 | 0.63 |
| 4 | 0.57 | 0.57 | 0.56 | 0.49 | 0.50 |
| 6 | 0.45 | 0.46 | 0.46 | 0.41 | 0.43 |

The heat exchanger for medical treatment of this invention comprises a cylindrical blood passing space and a multiplicity of heat-exchanging tubes disposed inside the blood passing space in the longitudinal direction of the blood passing space and provided with an inner space watertightly separated from the blood passing space and effecting exchange of heat between the blood being passed through the blood passing space and a heat-exchanging medium being passed through the inner spaces of the heat-exchanging tubes through the medium of walls of the heat-exchanging tubes and this heat exchanger is characterized by the fact that a blood inlet tube for introducing blood into the blood passing space and a blood outlet tube for discharging blood from within the blood passing space are extended inwardly from outside substantially along straight lines perpendicular to the longitudinal direction of the blood passing space and tangent to the peripheral plane of the blood passing space and communicating with the blood passing space as described above. It is, therefore, capable of causing the blood flowing through the blood passing space to be uniformly distributed within the blood passing space, effecting uniform exchange of heat on the entire blood passed through the heat exchanger, and exhibiting stable performance without exerting any adverse effect upon the blood components even when the temperature distribution of the blood is dispersed and the exchange of heat consequently occurs excessively or insufficiently.

The heat exchanger for medical treatment of the present invention is produced by causing a multiplicity of heat-exchanging tubes to be disposed as mutually separated inside a cylindrical housing possessing closed opposite ends in the longitudinal direction of the housing, partition walls disposed at the opposite end parts of the heat-exchanging tubes to hold the heat-exchanging tubes fast watertightly on the lateral wall of the housing without closing the openings of the heat-exchanging tubes and, at the same time, to partition the interior of the housing into three spaces, a blood inlet tube and a blood outlet tube extended inwardly from outside substantially along straight lines perpendicular to the longitudinal direction of the housing and tangent to the peripheral surface of the housing to communicate with a blood passing space formd in the central part of the housing by the two partition walls, the lateral wall of the housing, and the outer walls of the heat-exchanging tubes, and a heat-exchanging medium inlet tube to communicate with one of two heat-exchanging medium passing spaces formed at the end parts of the housing communicating with the inner spaces of the heat-exchanging tubes watertightly separated from the blood passing space and a heat-exchanging medium outlet tube to communicate with the other heat-exchanging medium passing space. It enjoys compactness of construction and high performance and, therefore, can be advantageously used as integrated with an oxygenator, for example. It is enabled to effect the exchange of heat with improved efficiency when the blood inlet tube communicates with the blood passing space near one of the partition walls and the blood outlet tube communicates with the blood passing space near the other partition wall and further the blood inlet tube and the blood outlet tube assume a positional relation such that they are rotated from each other in an angle of about 180° around the peripheral surface of the blood passing space.

The heat exchanger for medical treatment of this invention comprises a cylindrical blood passing space and a multiplicity of heat-exchanging tubes disposed inside the blood passing space in the longitudinal direction of the blood passing space and provided with an inner space watertightly separated from the blood passing space and effecting exchange of heat between the blood being passed through the blood passing space and a heat-exchanging medium being passed through the inner spaces of the heat-exchanging tubes through the medium of walls of the heat-exchanging tubes and this heat exchanger is characterized by the fact that a blood inlet tube for introducing blood into the blood passing space and a blood outlet tube for discharging blood from the blood passing space are severally extended inwardly from outside substantially along straight lines perpendicular to the longitudinal direction of the blood passing space and tangent to the peripheral place of the blood passing space and allowed to communicate with the blood passing space and said heat-exchanging tubes are disposed as uniformly separated mutually throughout the entire blood passing space except for an empty space portion formed by extending in the axial direction of the blood passing space a portion enclosed in the shape of a how possessing a chord substantially parallel to and equal to or slightly longer than a line segment connecting two points of intersection between two inner peripheral lines of the blood inlet tube and the circumference of the blood passing space in a cross section perpendicular to the axis of the blood passing space inclusive of the axial line of the blood inlet tube and an empty space portion formed by extending in the axial direction of the blood passing space a portion enclosed in the shape of a bow possessing a chord substantially parallel to and equal to or slightly longer than a line segment connecting two points of intersection between two inner peripheral lines of the blood outlet tube and the circumference of the blood passing space in a cross section perpendicular to the axis of the blood passing space inclusive of the axial line of the blood outlet tube. It enjoys compactness of construction and high performance and, therefore, can be advantageously used as integrated with an oxygenator, for example. It is enabled to effect the exchange of heat with improved efficiency and enabled to curb the pressure loss during the course of blood passage when the blood inelet tube communicates with the blood passing space near one of the partition walls and the blood outlet tube communicates with the blood passing space near the other partition wall and further the blood inlet tube and the blood outlet tube assume a positional relation such that they are rotated from each other in an angle of about 180° around the peripheral surface of the blood passing space.

The heat exchanger for medical treatment of this invention is produced by causing a multiplicity of heat-exchanging tubes to be disposed as mutually separated inside a cylindrical housing possessing closed opposite ends in the longitudinal direction of the housing, partition wall disposed at the opposite end parts of the heat-exchanging tubes to hold the heat-exchanging tubes fast watertightly on the lateral wall of the housing without closing the openings of the heat-exchanging tubes and, at the same time, partition the interior of the housing into three spaces, a blood inlet tube and a blood outlet tube to communicate with a blood passing space formed in the central part of the housing by the two partition walls, the lateral wall of the housing, and the outer walls of the heat-exchanging tubes, and a heat-exchanging medium inlet tube to communicate with one of two heat-exchanging medium passing spaces formed at the end parts of the housing communicating with the inner spaces of the heat-exchanging tubes watertightly separated from the blood passing space and a heat-exchanging medium outlet tube to communicate with the other heat-exchanging medium passing space. It enjoys compactness of construction and high performance and, therefore, can be advantageously used as integrated with an oxygenator, for example. It is enabled to effect the exchange of heat with improved efficiency when the blood inlet tube communicates with the blood passing space near one of the partition walls and the blood outlet tube communicates with the blood passing space near the other partition wall and further the blood inlet tube and blood outlet tube assume a positional relation such that they are rotated from each other in an angle of about 180° around the peripheral surface of the blood passing space and the two empty space portions destitute of heat-exchanging tubes in the blood passing space occupy a total volume of less than 40% of the volume of the blood passing space.

The heat exchanger of this invention comprises a cylindrical housing possessing a blood inlet and a blood outlet, a multiplicity of slender heat-exchanging tubes accommodated within the cylindrical housing, partition walls adapted to fix the opposite end parts of the slender heat-exchanging tubes watertightly to the cylindrical housing and partition the interior of the housing into a blood chamber communicating with the blood outlet and the blood inlet and a heat-exchanging medium chamber formed by the tube interiors, and a medium inlet and a medium outlet communicating with the heat-exchanging medium chamber and this heat exchanger further comprises a rib formed on the inner wall surface of the housing as extended parallelly to the slender tubes opposed to the inner wall surface and adapted to retard the flow of blood between the slender tubes and the inner wall surface of the housing. Particularly since the rib is formed on the inner wall surface of the housing, the blood flowing along the inner wall surface of the housing collides against the rib and then advances in the direction of the spaces intervening between the bundle of slender tubes. Thus, the blood flowing along the inner wall surface of the housing and reaching the blood outlet without undergoing sufficient exchange of heat can be decreased and the efficiency of exchange of heat can be improved.

The heat exchanger of this invention comprises an integrally molded cylindrical housing possessing a heat-exchanging medium inlet port disposed at one end part thereof, a heat-exchanging medium outlet port disposed at the other end part thereof, and a blood inlet port and a blood outlet port disposed at positions between the medium inlet port and the medium outlet port, a multiplicity of slender heat-exchanging tubes accommodated within the housing, partition walls adapted to fix the opposite end parts of the slender tubes watertightly to the cylindrical housing and partition the interior of the housing into a blood chamber communicating with the blood outlet port and the blood inlet port and a heat-exchanging medium chamber formed inside the tubes and adapted to communicate with the medium inlet port and the medium outlet port, and seal members serving to seal the opposite end parts of the housing. Since the heat-exchanging medium inlet port and outlet port are integrally formed with the housing, these inlet port and outlet port can be present at desired positions selected in the housing for each attachment of circuits, for example, during the formation of the housing and the partition walls for watertightly fixing the slender tubes in the housing can be fastened watertightly to the housing infallibly and the otherwise possible leakage of the heat-exchanging medium between the partition walls and the housing can be precluded.

The method for the production of the heat exchanger of this invention comprises the steps of forming a cylindrical housing possessing heat-exchanging medium ports disposed one each at the opposite end parts thereof and a blood inlet port and a blood outlet port disposed at positions between the medium ports, attaching a first sealing member at a position between those of the medium ports and the blood ports which are located at one end part of the cylindrical housing, inserting through the other end part of the cylindrical housing into the cylindrical housing a slender tube distributing device possessing a multiplicity of holes for insertion of slender heat-exchanging tubes and a multiplicity of slender heat-exchanging tubes, attaching a second sealing member at a position between those of the medium ports and the blood ports which are located at the other end part of the cylindrical housing, injecting a potting compound through the blood port on one end part side and the blood port on the other end part side of the cylindrical housing with the end parts of the slender heat-exchanging tubes kept in a closed state thereby forming partition walls for fixing the opposite end parts of the slender heat-exchanging tubes to the cylindrical housing, removing the first sealing member and the second sealing member, and fitting seal members one each to the opposite ends of the cylindrical housing. By this method, the heat exchanger of this invention described above can be easily produced.

The heat exchanger for medical treatment of the present invention comprises a housing for enclosing a closed empty space therewith and heat-exchanging tubes disposed inside the housing and provided each with an inner space watertightly separated from the closed empty space and effecting exchange of heat between a first fluid passed through the inner spaces of the heat-exchanging tubes and a second fluid passed through the closed empty space of the housing through the medium of walls of the heat-exchanging tubes and this heat exchanger is characterized by the fact that a heat-exchanging medium inlet port and a heat-exchanging medium outlet port for causing the first fluid or the second fluid intended as a heat-exchanging medium to be respectively introduced into and discharged from the inner spaces of the heat-exchanging tubes disposed inside the housing or the closed empty space of the housing are extended from the outer wall surface of the housing with flexible tubes. When the heat-exchanging medium inlet port and the heat-exchanging medium outlet port are connected to the connection tube, for example, of the heat-exchanging medium temperature controller, this connection can be easily attained because the heat exchanger and the heat-exchanging medium temperature controller are given a generous allowance with respect to their relative layout. If the positional relation between the heat exchanger and the heat-exchanging medium temperature controller is varied during the course of operation, there is no possibility of their connection being dissolved. The possible leakage of the heat-exchanging medium during the recovery of the blood can be precluded by clamping the flexible connection tube. The heat exchanger is very safe and easy to handle.

What is claimed is:

1. A method for manufacturing a heat exchanger for blood, said method comprising the steps of:

preparing a housing having first and second open ends, and first and second blood ports on a peripheral wall of said housing;

separately preparing an arranging member having a plurality of through openings for receiving therein heat-exchanging tubes so that said heat-exchanging tubes are arranged to be substantially parallel to each other;

arranging a first provisionally closing member in said housing near said first open end thereof;

inserting said arranging member into said housing so as to be separated from said first provisionally closing member by a predetermined distance to form a space therebetween;

inserting said heat-exchanging tubes into said through openings of said arranging member so that one ends of said heat-exchanging tubes come into contact with said first provisionally closing member;

arranging a second provisionally closing member in said housing near said second open end thereof so as to come into contact with other ends of said heat-exchanging tubes;

forming a first partition wall for supporting said one ends of said heat-exchanging tubes by injecting a potting compound into said space through one of said first and second blood ports and allowing the potting compound to solidify;

removing said second provisionally closing member and said arranging member from said housing;

rearranging said second provisionally closing member in said housing so as to come into contact with said other ends of said heat-exchanging tubes;

forming a second partition wall for supporting said other ends of said heat-exchanging tubes by injecting a potting compound into said housing through the other of said first and second blood ports and allowing the potting compound to solidify;

then removing said first and second provisionally closing members from said housing; and then forming a pair of heat-exchanging medium chambers at opposite end portions of said housing so as to communicate with each other through said heat exchanging tubes.

2. A method according to claim 1, wherein said potting compound is made of a material selected from the group consisting of polyurethanes and silicone rubbers.

3. A method according to claim 1, wherein said first and second provisionally closing members are made of a material which is difficult to adhere to said potting compound.

4. A method according to claim 1, wherein said housing has a heat-exchanging medium inlet port and a heat-exchanging medium outlet port on the peripheral wall thereof at opposite end portions thereof.

5. A method for manufacturing a heat exchanger for blood, said method comprising the steps of:
   preparing a housing having first and second open ends, and first and second blood ports on a peripheral wall of said housing;
   separately preparing an arranging member having a plurality of through openings for receiving therein heat-exchanging tubes so that said heat-exchanging tubes are arranged to be substantially parallel to each other;
   arranging a first provisionally closing member in said housing near said first open end thereof;
   inserting said arranging member into said housing so as to be separated from said first provisionally closing member by a predetermined distance to form a space therebetween;
   inserting said heat-exchanging tubes into said through openings of said arranging member so that one ends of said heat-exchanging tubes come into contact with said first provisionally closing member;
   arranging a second provisionally closing member in said housing near said second open end thereof so as to come into contact with other ends of said heat-exchanging tubes;
   forming a first partition wall for supporting said one ends of said heat-exchanging tubes by injecting a potting compound into said space through one of said first and second blood ports and allowing the potting compound to solidify;
   removing said first and second provisionally closing members and said arranging member from said housing, and reversing the positions of said first and second provisionally closing members in said housing;
   forming a second partition wall for supporting said other ends of said heat-exchanging tubes by injecting a potting compound into said housing through the other of said first and second blood ports and allowing the potting compound to solidify;
   removing said second provisionally closing member from said housing; and
   forming a pair of heat-exchanging medium chambers at opposite end portions of said housing so as to communicate with each other through said heat exchanging tubes.

6. A method according to claim 5, wherein said potting compound is made of a material selected from the group consisting of polyurethanes and silicone rubbers.

7. A method according to claim 5, wherein of said first and second provisionally closing members are made a material which is difficult to adhere to said potting compound.

8. A method according to claim 5, wherein said potting compound is made of a polyurethane and an elastic member serving as said first provisionally closing member is made of a silicone rubber.

9. A method according to claim 5, wherein said potting compound is made of a silicone rubber and said elastic member serving as said first provisionally closing member is made of a polyurethane.

10. A method according to claim 5, wherein said housing has a heat-exchanging medium inlet port and a heat-exchanging medium outlet port on the peripheral wall thereof at opposite end portions thereof.

11. A method for manufacturing a heat exchanger for blood, said method comprising the steps of:
    preparing a housing having first and second open ends, and first and second blood ports on a peripheral wall of said housing;
    separately preparing an arranging member having a plurality of through openings for receiving therein heat-exchanging tubes so as to allow said heat-exchanging tubes to be arranged substantially parallel to each other;
    arranging a first provisionally closing member in said housing near said first open end thereof;
    inserting said arranging member into said housing so as to be separated from said first provisionally closing member by a predetermined distance;
    inserting said heat-exchanging tubes into said through openings of said arranging member so that one ends of said heat-exchanging tubes come into contact with said first provisionally closing member;
    arranging a second provisionally closing member in said housing near said second open ends thereof so as to come into contact with other ends of said heat-exchanging tubes;
    forming a first partition wall for supporting said one ends of said heat-exchanging tubes by injecting a potting compound into said housing through one of said first and second blood ports and allowing the potting compound to solidify;
    forming a second partition wall for supporting said other ends of said heat-exchanging tubes by injecting a potting compound into said housing through the other of said first and second blood ports and allowing the potting compound to solidify;
    removing said first and second provisionally closing members from said housing; and
    forming a pair of heat-exchanging medium chambers at opposite end portions of said housing so as to communicate with each other through said heat exchanging tubes.

12. A method according to claim 11, wherein said arranging member is made of a material selected from the group consisting of metals and synthetic resins.

13. A method according to claim 11, wherein said potting compound is made of a material selected from the group consisting of polyurethanes and silicone rubbers.

14. A method according to claim 11, wherein said first and second provisionally closing members are made of a material which is difficult to adhere to said potting compound.

15. A method according to claim 11, wherein said housing has a heat-exchanging medium inlet port and a heat-exchanging medium outlet port on the peripheral wall thereof at opposite end portions thereof.

16. A method for manufacturing a heat exchanger for blood, said method comprising the steps of:

preparing a housing having first and second open ends, and first and second blood ports on a peripheral wall of said housing;

separately preparing an arranging member having a plurality of through openings for receiving therein heat-exchanging tubes so that said heat-exchanging tubes are arranged to be substantially parallel to each other;

arranging a first provisionally closing member in said housing near said first open end thereof;

inserting said arranging member into said housing so as to be separated from said first provisionally closing member by a predetermined distance;

inserting said heat-exchanging tubes into said through openings of said arranging member so that one ends of said heat-exchanging tubes come into contact with said first provisionally closing member;

arranging a second provisionally closing member in said housing near said second open end thereof so as to come into contact with other ends of said heat-exchanging tubes;

forming a first partition wall for supporting said one ends of said heat-exchanging tubes by injecting a potting compound into said housing through one of said first and second blood ports and allowing the potting compound to solidify;

reversing the positions said first and second provisionally closing members in said housing;

forming a second partition wall for supporting said other ends of said heat-exchanging tubes by injecting potting compound into said housing through the other of said first and second blood ports to allow the potting compound to solidify;

removing said second provisionally closing member from said housing; and forming a pair of heat-exchanging medium chambers at opposite end portions of said housing so as to communicate with each other through said heat exchanging tubes.

17. A method according to claim 16, wherein said arranging member is made of a material selected from the group consisting of metals and synthetic resins.

18. A method according to claim 16, wherein said potting compound is made of a material selected from the group consisting of polyurethanes and silicone rubbers.

19. A method according to claim 16, wherein said first and second provisionally closing members are made of a material which is difficult to adhere to said potting compound.

20. A method according to claim 16, wherein said potting compound is made of a polyurethane and said elastic member serving as said first provisionally closing member is made of a silicone rubber.

21. A method according to claim 16, wherein said potting compound is made of a silicone rubber and said elastic member serving as said first provisionally closing member is made of a polyurethane.

22. A method according to claim 5, wherein said first provisionally closing member comprises an elastic member.

23. A method according to claim 5, wherein said removing step comprises removing both of said first and second provisionally closing members from said housing.

24. A method according to claim 16, wehrin said first provisionally closing member comprises an elastic member.

25. A method according to claim 16, wherein said removing step comprises removing both of said first and second provisionally closing members from said housing.

* * * * *

UNITED STATES PATENT AND TRADEMARK OFFICE
CERTIFICATE OF CORRECTION

Figure 1:
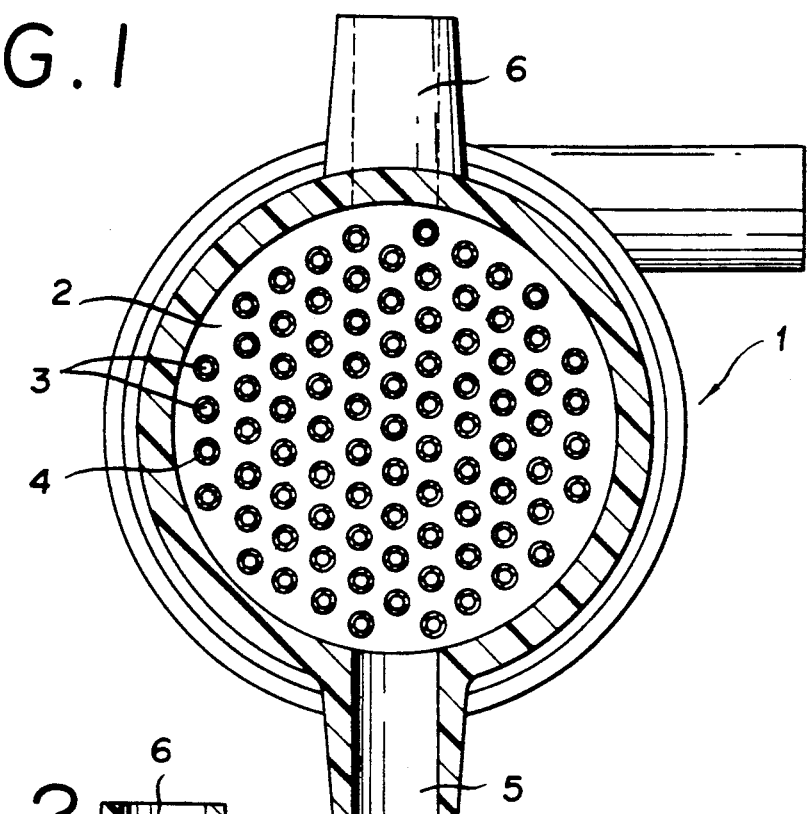
FIG. 1 is a cross section taken through a conventional heat exchanger perpendicularly to the axis thereof to illustrate the construction thereof.
Figure 2:
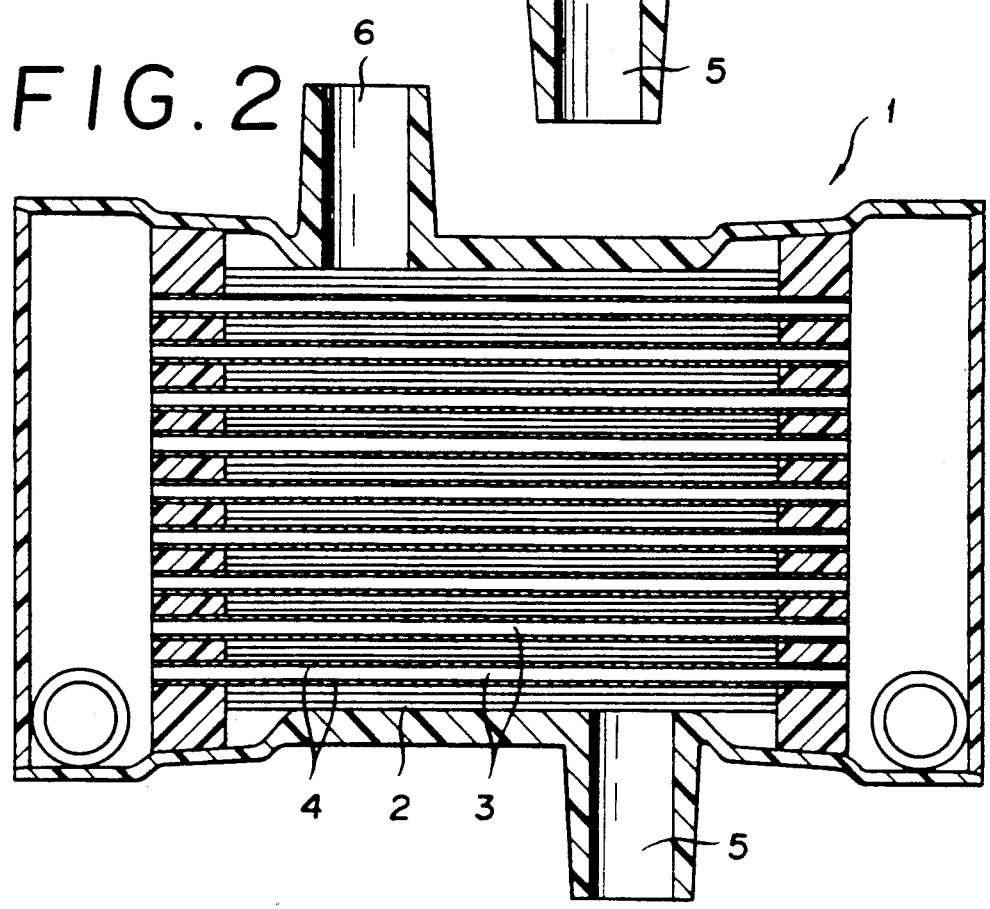
FIG. 2 is a cross section taken through the conventional heat exchanger in the directon of the axis thereof.
Figure 11B:
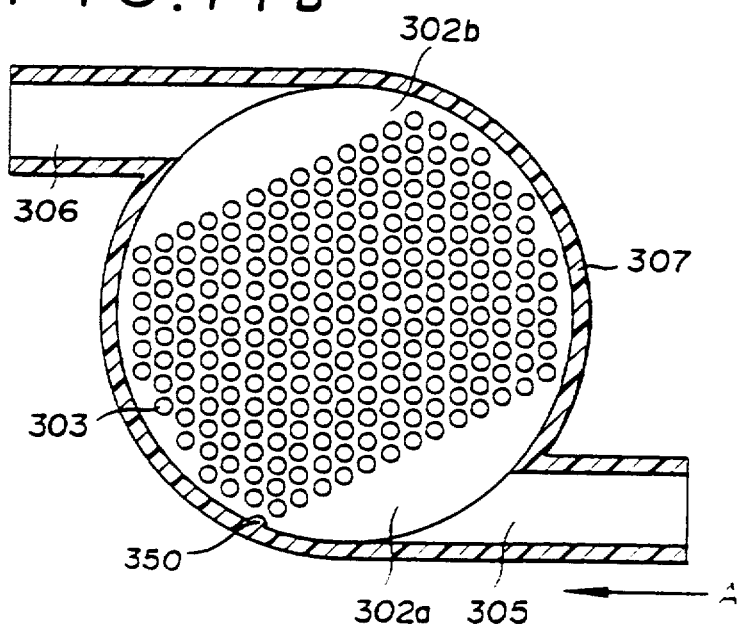
Figure 12:
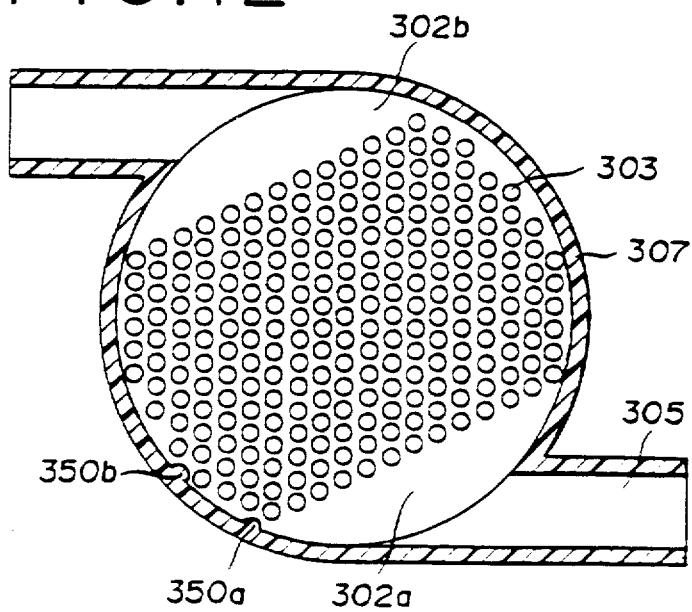

PATENT NO. : 5,294,397
DATED : March 15, 1994
INVENTOR(S) : OSHIYAMA et al It is certified that error appears in the above-identified patent and that said Letters Patent is hereby corrected as shown below:

In the Drawings, Figs. 1, 2 and 11 should be deleted and replaced with the attached sheets.

Column 4, line 10, start a new paragraph with --This--

Column 5, line 15, start a new paragraph with --This--

Column 6, line 19, "partitin" should read --partition--

Column 9, line 9, "partially" should be --partial--

Column 24, line 58, "161" should be --162--

Column 24, line 59, "162" should be --161--

Column 25, line 34, "161" should be --164--

Column 31, line 47, "how" should be --bow--

Column 32, line 1, "inelet" should be --inlet--

Signed and Sealed this

Sixth Day of June, 1995

Attest:

BRUCE LEHMAN

*Attesting Officer*     *Commissioner of Patents and Trademarks*

PRIOR ART